US012285322B2

(12) United States Patent
Wade et al.

(10) Patent No.: US 12,285,322 B2
(45) Date of Patent: *Apr. 29, 2025

(54) ABSORBENT ARTICLES WITH ELASTICS IN MULTIPLE LAYERS

(71) Applicant: The Procter & Gamble Company, Cincinnati, OH (US)

(72) Inventors: Sarah Marie Wade, Springfield Township, OH (US); Tina Marie Glahn, West Chester, OH (US); Gary Dean Lavon, Liberty Township, OH (US); Diana Woehnl Juratovac, Columbus, OH (US); Kaoru Ishihara, West Chester, OH (US); Masaharu Nishikawa, Cincinnati, OH (US); Ronald Joseph Zink, Blue Ash, OH (US); Anna Elizabeth Macura, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/408,989

(22) Filed: Jan. 10, 2024

(65) Prior Publication Data

US 2024/0139036 A1    May 2, 2024

Related U.S. Application Data

(63) Continuation of application No. 17/959,338, filed on Oct. 4, 2022, now Pat. No. 11,903,803, which is a
(Continued)

(51) Int. Cl.
*A61F 13/49*  (2006.01)
*A61F 13/56*  (2006.01)
*A61F 13/64*  (2006.01)

(52) U.S. Cl.
CPC .. *A61F 13/49011* (2013.01); *A61F 13/49012* (2013.01); *A61F 13/49019* (2013.01);
(Continued)

(58) Field of Classification Search
CPC ...... A61F 13/490007; A61F 13/490009; A61F 13/49011; A61F 13/49012;
(Continued)

(56) References Cited

U.S. PATENT DOCUMENTS 3,848,594 A    11/1974  Buell
4,662,875 A    5/1987   Hirotsu
(Continued)

FOREIGN PATENT DOCUMENTS

JP    H10179635 A    7/1998
JP    2001252303 A5  11/2006
(Continued)

OTHER PUBLICATIONS

12895D EPO Search Report and Opinion for 24161819.8 dated Jun. 14, 2024, 8 pages.
(Continued)

*Primary Examiner* — Michele Kidwell
(74) *Attorney, Agent, or Firm* — Charles R. Matson

(57) ABSTRACT

Absorbent articles that include elastics in multiple layers are disclosed herein.

10 Claims, 20 Drawing Sheets

Related U.S. Application Data continuation of application No. 16/881,050, filed on May 22, 2020, now Pat. No. 11,491,056, which is a continuation of application No. 15/820,552, filed on Nov. 22, 2017, now Pat. No. 10,695,234, which is a continuation of application No. 15/159,142, filed on May 19, 2016, now Pat. No. 9,867,741, which is a continuation of application No. 14/681,140, filed on Apr. 8, 2015, now Pat. No. 9,370,453, which is a continuation of application No. 13/893,889, filed on May 14, 2013, now Pat. No. 9,023,008.

(60) Provisional application No. 61/646,999, filed on May 15, 2012.

(52) U.S. Cl.
CPC .... *A61F 13/4906* (2013.01); *A61F 13/49061* (2013.01); *A61F 13/5622* (2013.01); *A61F 13/64* (2013.01); *A61F 2013/49088* (2013.01); *A61F 2013/49098* (2013.01); *F04C 2270/0421* (2013.01)

(58) Field of Classification Search
CPC .......... A61F 13/49014; A61F 13/49019; A61F 13/4902; A61F 13/49025; A61F 13/4906; A61F 2013/5677; A61F 2013/49042; A61F 2013/49039
See application file for complete search history.

(56) References Cited

U.S. PATENT DOCUMENTS

| | | |
|---|---|---|
| 4,846,815 A | 7/1989 | Scripps |
| 4,894,060 A | 1/1990 | Nestegard |
| 4,946,527 A | 8/1990 | Battrell |
| 5,151,092 A | 9/1992 | Buell |
| 5,221,274 A | 6/1993 | Buell |
| 6,142,985 A | 11/2000 | Feist |
| 6,169,151 B1 | 1/2001 | Waymouth et al. |
| 6,258,077 B1 | 7/2001 | Buell et al. |
| 6,410,129 B2 | 6/2002 | Zhang |
| 6,428,526 B1 | 8/2002 | Heindel |
| 6,432,098 B1 | 8/2002 | Kline |
| 6,447,497 B1 | 9/2002 | Olson |
| 6,518,378 B2 | 2/2003 | Waymouth et al. |
| 6,555,643 B1 | 4/2003 | Rieger |
| 6,559,262 B1 | 5/2003 | Waymouth et al. |
| 7,087,287 B2 | 8/2006 | Curro et al. |
| 7,819,853 B2 | 10/2010 | Desai |
| 7,890,090 B2 | 2/2011 | Hansen et al. |
| 7,947,029 B2 | 5/2011 | Saito |
| 7,977,528 B2 | 7/2011 | Vargo et al. |
| 8,475,424 B2 | 7/2013 | Fujimoto et al. |
| 9,023,008 B2 | 5/2015 | Wade et al. |
| 9,023,088 B2 | 5/2015 | Voisard et al. |
| 9,370,453 B2 | 6/2016 | Wade et al. |
| 9,421,137 B2 | 8/2016 | Lavon |
| 9,867,741 B2 | 1/2018 | Wade et al. |
| 10,695,234 B2 | 6/2020 | Wade et al. |
| 11,491,056 B2 | 11/2022 | Wade et al. |
| 11,903,803 B2 | 2/2024 | Wade |
| 2004/0092677 A1 | 5/2004 | Hanke et al. |
| 2005/0000628 A1 | 1/2005 | Norrby |
| 2005/0004549 A1 | 1/2005 | Maas et al. |
| 2005/0004594 A1 | 1/2005 | Nool et al. |
| 2005/0131374 A1 | 6/2005 | Otsubo et al. |
| 2005/0137563 A1 | 6/2005 | Van Gompel et al. |
| 2005/0164587 A1 | 7/2005 | Melik |
| 2006/0173436 A1 | 8/2006 | Krautkramer et al. |
| 2007/0066952 A1 | 3/2007 | Beck et al. |
| 2009/0005751 A1 | 1/2009 | Shirai et al. |
| 2009/0177176 A1 | 7/2009 | Saito |
| 2009/0258210 A1 | 10/2009 | Iyad |
| 2013/0310789 A1 | 11/2013 | Wade et al. |
| 2016/0331601 A1 | 11/2016 | Lavon et al. |
| 2018/0092784 A1 | 4/2018 | Wade |
| 2020/0281780 A1 | 9/2020 | Wade et al. |
| 2023/0026296 A1 | 1/2023 | Wade et al. |

FOREIGN PATENT DOCUMENTS

| | | |
|---|---|---|
| JP | 2010082364 A | 4/2010 |
| WO | 9309739 A1 | 5/1993 |
| WO | 2005004766 A1 | 1/2005 |
| WO | 2006078465 A2 | 7/2006 |
| WO | 2006110442 A1 | 10/2006 |
| WO | 2007133127 A1 | 11/2007 |
| WO | 2011048512 A2 | 4/2011 |
| WO | 2011048513 A2 | 4/2011 |
| WO | 2011080655 A2 | 7/2011 |

OTHER PUBLICATIONS

12895 PCT International Search Report and Written Opinion for PCT/US2013/040897 dated Oct. 23, 2013, 10 pages.
All Office Actions, U.S. Appl. No. 13/893,889, filed May 14, 2013.
All Office Actions, U.S. Appl. No. 14/681,140, filed Apr. 8, 2015.
All Office Actions, U.S. Appl. No. 15/159,142, filed May 19, 2016.
All Office Actions, U.S. Appl. No. 15/820,552, filed Nov. 22, 2017.
All Office Actions; U.S. Appl. No. 16/881,050, filed May 22, 2020.
All Office Actions; U.S. Appl. No. 17/959,338, filed Oct. 4, 2022.
12895-EP Notice of Opposition for 13727694.5 dated Jan. 22, 2025, 30 pages.

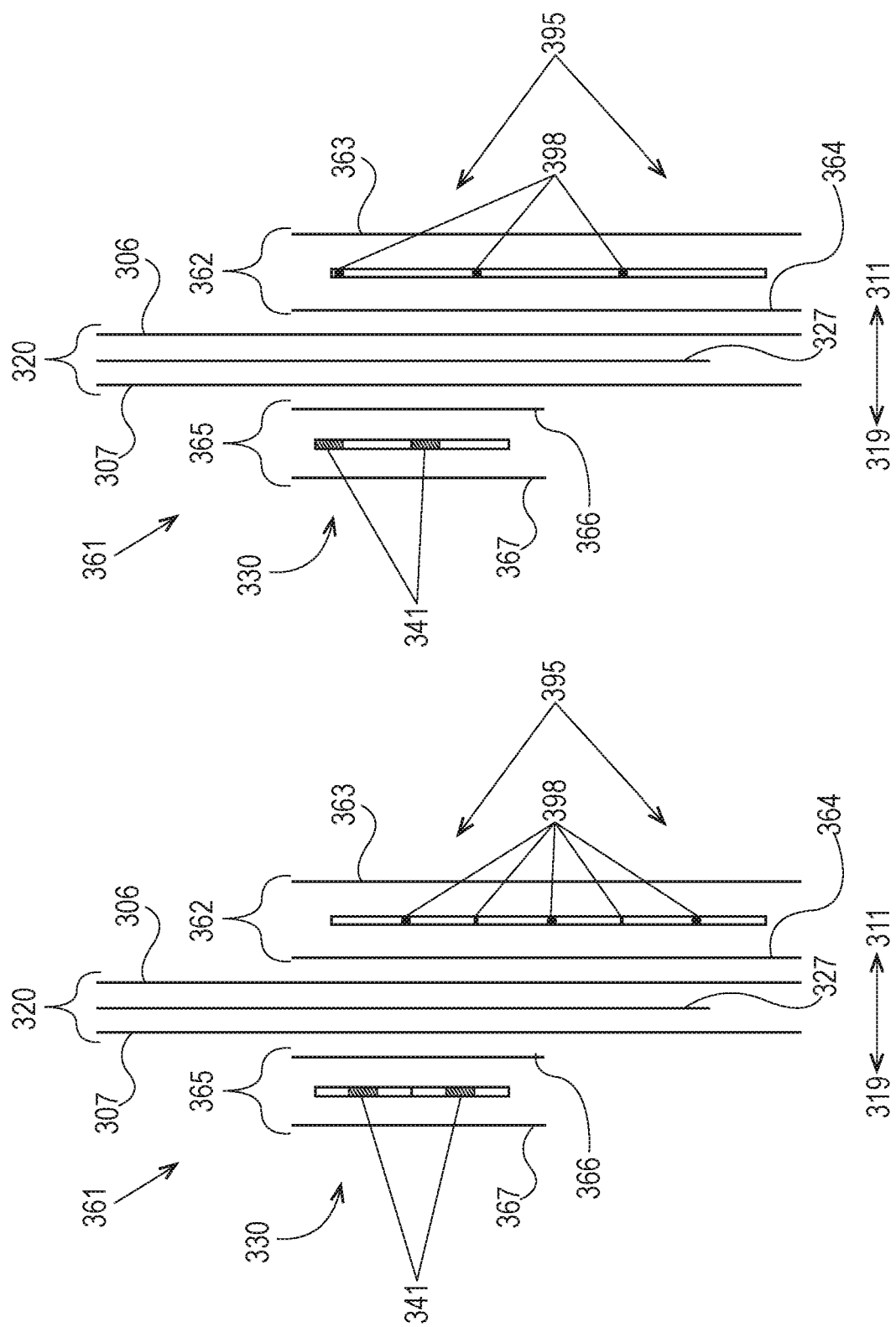

ABSORBENT ARTICLES WITH ELASTICS IN MULTIPLE LAYERS

CROSS REFERENCE TO RELATED REFERENCE

This application is a continuation of U.S. Nonprovisional application Ser. No. 17/959,338, filed on Oct. 4, 2022, which is a continuation of U.S. Nonprovisional application Ser. No. 16/881,050, filed on May 22, 2020, which is a continuation of U.S. Nonprovisional application Ser. No. 15/820,552, filed on Nov. 22, 2017, which is a continuation of U.S. Nonprovisional application Ser. No. 15/159,142, filed May 19, 2016, which is a continuation of U.S. Nonprovisional application Ser. No. 14/681,140, filed Apr. 8, 2015, which is a continuation of U.S. Nonprovisional application Ser. No. 13/893,889, filed May 14, 2013, which claims the benefit of U.S. Provisional Application Ser. No. 61/646,999, filed May 15, 2012, the entirety of which are incorporated by reference herein.

FIELD

In general, embodiments of the present disclosure relate to absorbent articles that are disposable and wearable. In particular, embodiments of the present disclosure relate to disposable wearable absorbent articles with elastics in multiple layers.

BACKGROUND

Disposable wearable absorbent articles include disposable diapers and disposable incontinence undergarments (e.g., adult incontinence products). A disposable wearable absorbent article can receive and contain bodily waste while being worn by a wearer. Such articles can be made with various materials in a number of configurations. The design of a disposable wearable absorbent article can affect the way that the article performs while it is being worn.

Elastic materials can be configured as various elastic structures in disposable wearable absorbent articles. These elastic structures can function in different ways to provide various benefits to the wearer. For example, lower force elastics or elastics that are spaced apart can be configured as shaping elastics. Shaping elastics can assist in providing a conforming fit and distributing contact forces over the wearer's skin. As another example, higher force elastics or elastics that are grouped closer together can be configured as anchoring elastics. Anchoring elastics can assist in holding the article in place on the wearer by transferring loads from the article to particular parts of the wearer's body.

Unfortunately, when a disposable wearable absorbent article includes different elastic structures, those structures may not work well together. For example, if a disposable wearable absorbent article includes both shaping elastics and anchoring elastics, and those different elastic structures are not allowed to act somewhat independently from each other, then their functions may be compromised. If the anchoring elastics transfer excessive loads to the region comprising the shaping elastics, they may concentrate forces against the wearer's skin, causing discomfort and red marking. If the shaping elastics compromise the loads created by the anchoring elastics, then the anchoring elastics may not effectively transfer loads to intended parts of the wearer's body, potentially allowing the article to sag. If a disposable wearable absorbent article includes elastic structures that do not work well together, then the article may feel uncomfortable, look unattractive, and perform poorly while it is worn by a wearer.

SUMMARY

In one aspect, an absorbent article has a center chassis including a topsheet, a backsheet and an absorbent core. The absorbent article includes a front waist region and a front waist edge, a front inner belt portion disposed in the front waist region, a front outer belt portion disposed in the front waist region, a first plurality of elastics disposed in the front inner belt portion and inward of the front outer belt portion, and a second plurality of elastics disposed in the front outer belt portion and outward of the front inner belt portion, wherein at least a portion of at least one of the first and second pluralities of elastics comprise anchoring elastics, at least a portion of at least one of the first and second pluralities of elastics comprise shaping elastics, and the absorbent article is disposable and wearable.

In another aspect, an absorbent article has a center chassis including a topsheet, a backsheet and an absorbent core. The absorbent article includes a back waist region and a back waist edge, a back inner belt portion disposed in the back waist region, a back outer belt portion disposed in the back waist region, a first plurality of elastics disposed in the back inner belt portion and inward of the back outer belt portion, and a second plurality of elastics disposed in the back outer belt portion and outward of the back inner belt portion, wherein at least a portion of at least one of the first and second pluralities of elastics comprise anchoring elastics, at least a portion of at least one of the first and second pluralities of elastics comprise shaping elastics, and the absorbent article is disposable and wearable.

In yet another aspect, an absorbent article has a center chassis including a topsheet, a backsheet and an absorbent core. The absorbent article includes a front waist region and a front waist edge, a back waist region and a back waist edge, a front inner belt portion disposed in the front waist region, a front outer belt portion disposed in the front waist region, a back inner belt portion disposed in the back waist region, a back outer belt portion disposed in the back waist region, a first plurality of elastics disposed in the front inner belt portion and inward of the front outer belt portion, a second plurality of elastics disposed in the front outer belt portion and outward of the front inner belt portion, a third plurality of elastics disposed in the back inner belt portion and inward of the back outer belt portion, and a fourth plurality of elastics disposed in the back outer belt portion and outward of the back inner belt portion, wherein at least a portion of at least one of the first, second, third and fourth pluralities of elastics comprise anchoring elastics, at least a portion of at least one of the first, second, third and fourth pluralities of elastics comprise shaping elastics, and the absorbent article is disposable and wearable.

Additional aspects of the disclosure are defined by the claims of this patent.

BRIEF DESCRIPTION OF THE DRAWINGS

FIG. 3B illustrates an exploded cross-sectional side view of part of the front of the article of FIG. 3A, taken at a first sectional line.

FIG. 3C illustrates an exploded cross-sectional side view of part of the front of the article of FIG. 3A, taken at a second sectional line.

DETAILED DESCRIPTION

Figure 1A:
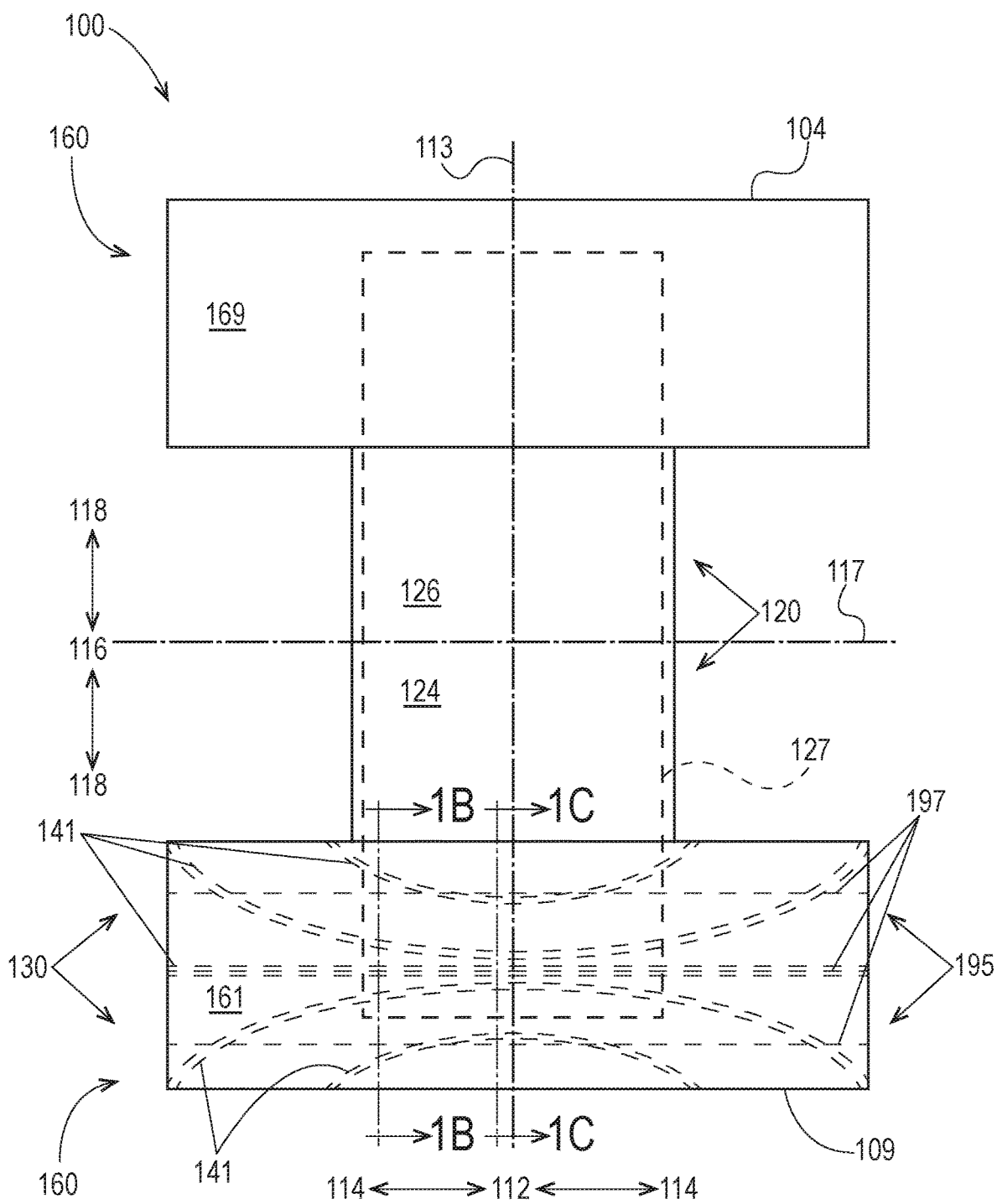
FIG. 1A illustrates a plan view of a belt type disposable wearable absorbent article, which includes a first embodiment of elastics in multiple layers.

Embodiments of the present disclosure include disposable wearable absorbent articles with different elastic structures that work well together. The different elastic structures may be separated into multiple layers. For example, a disposable wearable absorbent article can include shaping elastics and anchoring elastics, which are separated from each other by one or more layers of material. Since the shaping elastics are separated from the anchoring elastics, they can function independently of each other. The shaping elastics can at least assist in providing a conforming fit and distributing contact forces over the wearer's skin while the anchoring elastics can at least assist in holding the article in place on the wearer. As a result, the disposable wearable absorbent articles of the present disclosure can be easier to apply, feel comfortable, look attractive, and perform well while worn by wearers.

Absorbent articles include products for human sanitary protection, for human hygienic use, and the like. Some absorbent articles are wearable. A wearable absorbent article is configured to be worn on or around a lower torso of a body of a human wearer. Examples of wearable absorbent articles include diapers, training pants, and incontinence undergarments (including embodiments of each of these for people of all ages).

A disposable wearable absorbent article can include an absorbent core. Throughout the present disclosure, the term absorbent core refers to a part of a disposable wearable absorbent article configured to absorb bodily exudates (such as urine, menses, and feces) received into the article from a body of a wearer. An absorbent core can be configured in various ways, as will be understood by one of ordinary skill in the art. An absorbent core can include one or more absorbent materials, such as absorbent foams, highloft nonwovens, wood pulp and/or superabsorbent particles, and may include one or more additional compositions, materials, or structures for receiving, containing, storing, and/or treating bodily waste, as known in the art.

An absorbent core can be part of an absorbent assembly, comprising one or more layers such as a liquid-permeable topsheet, an acquisition layer, a distribution layer, a storage layer, and a liquid impermeable backsheet. Part, parts, or all of an absorbent core and/or part, parts, or all of an absorbent assembly may also include one or more of various structures, such as barrier leg cuffs, a feces containment compartment, a wetness indicator, fasteners for retaining the core within an article, disposal tapes, etc. Further, part, parts, or all of an absorbent core and/or part, parts, or all of an absorbent assembly may include one or more of compositions such as lotions, perfumes, and a sensate. An absorbent core and/or an absorbent assembly can be configured as a bucket-shaped absorbent assembly, a removable absorbent core or absorbent assembly, a replaceable absorbent core, etc.

A disposable wearable absorbent article can also include an outer cover. Throughout the present disclosure, the term outer cover refers to a part of a disposable wearable absorbent article forming an outer surface of the article (sometimes referred to as a backsheet), extending beyond the edges of the absorbent core, usually covering a significant portion of the buttocks of the wearer, and generally shaped to resemble the appearance of an undergarment. An outer cover can be configured in various ways, as described herein. In various embodiments, an outer cover can coincide with and/or define at least a portion of the chassis of a disposable wearable absorbent article.

Some absorbent articles are disposable. A disposable absorbent article is configured to be disposed of after a single use (e.g., not intended to be reused, restored, or laundered). Examples of disposable absorbent articles include disposable diapers, disposable training pants, disposable incontinence undergarments, as well as feminine care pads and liners.

Elastic materials can be configured as various elastic structures in disposable wearable absorbent articles. These elastic structures can function in different ways to provide various benefits to the wearer. For example, lower force elastics or elastics that are spaced apart can be configured as shaping elastics. Shaping elastics can at least assist in providing conforming fit and distributing contact forces over the wearer's skin. As another example, higher force elastics or elastics that are grouped closer together can be configured as anchoring elastics. Anchoring elastics can at least assist in holding the article in place on the wearer by transferring loads from the article to particular parts of the wearer's body.

Non-limiting types of elastic materials applicable for use in the embodiments disclosed herein include elastic strands, elastic ribbons, elastic films, elastic non-wovens, and combinations thereof. When the description details a plurality of elastics herein, it will be obvious to one skilled in the art that the term "plurality" refers to embodiments employing elastic strands and/or elastic ribbons or strips (as shown in the figure), however, in other embodiments, one or more elastic films or elastic non-wovens may take the place of the plurality of elastic strands and/or elastic ribbons.

The elastic material may be in the form of films, knitted fabrics, woven fibrous webs or nonwoven fibrous webs. In some embodiments, the elastic materials may be in the form of extensible nonwovens or webs comprising of polyolefinic fibers or filaments. Exemplary elastic materials are disclosed in U.S. Pat. Nos. 7,819,853; 7,087,287; and 6,410,129; and U.S. Patent Publication Nos. 2007/0287438; 2005/0164587; and 2009/0258210.

Suitable elastomeric compositions may be applied to a substrate in a fluid or fluid-like state to affect at least partial penetration into the substrate, thus, achieving sufficient bonding between the resulting elastomeric members and the substrate such that the composite resists delamination in the subsequent incremental stretching step. The elastomeric composition may have a melt viscosity from about 1 to about 150 Pa·s, preferably from about 5 to about 100 Pa·s, and more preferably from about 10 to about 80 Pa·s, at 175° C. and 1 $s^{-1}$ shear rate. Such elastomeric composition is suitable for use in the articles of the present invention.

Suitable elastomeric compositions comprise thermoplastic elastomers selected from the group consisting of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON® from the Shell Chemical Company of Houston, TX; SEPTON® from Kuraray America, Inc. of New York, NY; and VECTOR® from Dexco Chemical Company of Houston, TX. Commercially available metallocene-catalyzed polyolefins include EXXPOL® and EXACT® from Exxon Chemical Company of Baytown, TX; AFFINITY® and ENGAGE® from Dow Chemical Company of Midland, MI. Commercially available polyurethanes include ESTANE® from Noveon, Inc., Cleveland, OH. Commercial available polyether amides include PEBAX® from Atofina Chemicals of Philadelphia, PA. Commercially available polyesters include HYTREL® from E. I. DuPont de Nemours Co., of Wilmington, DE.

Applicable nonwoven webs may comprise multicomponent fibers. The multicomponent fibers will comprise a first component comprising a polypropylene composition having a melt flow rate of from about 100 to about 2000 grams per 10 minutes and a second component comprising a polymer composition having a melt flow rate lower than the melt flow rate of the first component. The first component comprises at least about 10% of a surface of the multicomponent fiber. Typically, the ratio of the first component to the second component is from about 10:90 to about 90:10. Preferably, the first component comprises at least about 50% of the surface of the multicomponent fiber and more preferably, the fiber is a bicomponent fiber with the first component being a sheath and the second component being a core. The polypropylene composition of the first component may comprise two or more different polypropylenes or a polypropylene and a different polymer. The second component will preferably have a melt flow rate of from about to about 80 grams per 10 minutes and may be a low melt flow rate polypropylene or any thermoplastic composition. Preferably, the melt flow rate of the first component is from about 100 to about 1000 grams per 10 minutes and the second component has a melt flow rate of about 10 to about 80 grams per 10 minutes. The nonwoven web may have a basis weight of from about 5 to about 100 gsm and may be produced by a spunbound process. The diameter of the fibers comprising the web will typically be from about 5 to about 50 microns. The nonwoven web may optionally comprise fibers other than the fibers comprising the polymer composition detailed above. The strain at peak load of the nonwoven web is preferably greater than 80% in at least one direction.

The elastomeric film may be formed in a single layer or in a multi-layer structure. The multilayer films may comprise two or more layers, at least one of the layers being elastomeric. Although an elastomeric layer is generally substantially joined to one or two skin layers, it is contemplated that multiple elastomeric layers may be utilized, each elastomeric layer being joined to one or two skin layers. Three-layer films preferably comprise a central elastomeric core that may comprise from about 10 to 90 percent of the total thickness of the film. The outer skin layers are generally, but not necessarily, identical and may comprise from about 5 to 45 percent of the total thickness of the film. Tie layers, when employed, may each comprise from about 5 to 10 percent of the total film thickness. In a three-layer film, core layer has opposed first and second sides, one side being substantially continuously joined to one side of each outer skin layer prior to the application of applied stress to the web.

A particularly preferred multilayer film has an elastomeric layer interposed between two skin layers. The elastomeric layer preferably comprises a thermoplastic elastomer comprised of a substantially continuous amorphous matrix, with glassy or crystalline domains interspersed throughout, the domains acting as effective physical crosslinks and hence enabling the material to exhibit an elastic memory when subjected to an applied strain and subsequently released. Preferred elastomeric materials include block copolymers and blends thereof, such as styrene-butadiene-styrene or other such common styrenic block copolymers as are generally available from the Shell Company under the trade name "KRATON." Similarly, polyolefinic materials such as polyethylene and polypropylene generally of densities below about 0.9 g/cc could likewise exhibit the necessary thermoplastic character and resultant elastic behavior. The skin layers preferably comprise any thermoplastic polymer, especially polyolefinic polymers such as polyethylene or polypropylene, generally of density greater than about 0.9 g/cc which are capable of thermoplastic processing into thin films. The skin layer should have sufficient adhesion to the elastomeric layer such that it will not completely delaminate either before or after stretching of the web. A preferred method to produce the multilayer polymeric film is coextrusion.

The elastomeric layer may provide the desired amount and force of recovery upon the relaxation of an elongating tension on the plastoelastic material, especially upon strain cycles following the initial shaping strain cycle. Many elastic materials are known in the art, including synthetic or natural rubbers (e.g., crosslinked polyisoprene, polybutadiene and their saturated versions (after hydrogenation), and polyisobutylene), thermoplastic elastomers based on multiblock copolymers, such as those comprising copolymerized rubber elastomeric blocks with polystyrene blocks (e.g., styrene-isoprene-styrene, styrene-butadiene-styrene, styrene-ethylene/butylene-styrene, styrene-ethylene/propylene-styrene, and styrene-butadiene/isoprene-styrene, including their hydrogenated and non-hydrogenated forms), thermoplastic elastomers based on polyurethanes (which form a hard phase that provides high mechanical integrity when dispersed in an elastomeric phase by anchoring the polymer chains together), polyesters, polyether amides, elastomeric polyethylenes, elastomeric polypropylenes, and combinations thereof. Some particularly suitable examples of elastic components include styrenic block copolymers, elastomeric polyolefins, and polyurethanes.

Other particularly suitable examples of elastic components include elastomeric polypropylenes. In these materials, propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra low density polypropylene), a metallocene polypropylene, and combinations thereof. Suitable polypropylene polymers including crystalline isotactic blocks and amorphous atactic blocks are described, for example, in U.S. Pat. Nos. 6,559,262, 6,518,378, and 6,169,151. Suitable isotactic polypropylene with stereoerrors along the polymer chain are described in U.S. Pat. No. 6,555,643 and EP 1 256 594 A1. Suitable examples include elastomeric random copolymers (RCPs) including propylene with a low level comonomer (e.g., ethylene or a higher α-olefin) incorporated into the backbone. Suitable elastomeric RCP materials are available under the names VISTAMAXX (available from ExxonMobil, Houston, TX) and VERSIFY (available from Dow Chemical, Midland, MI).

The embodiments of FIGS. 1A through 3E describe different types of disposable wearable absorbent articles with various embodiments of elastics in multiple layers.

FIG. 1A illustrates a plan view of a belt type disposable wearable absorbent article 100, which includes a first embodiment of elastics in multiple layers. FIG. 1A illustrates a plan view of a belt type disposable wearable absorbent article 100. The view of FIG. 1A illustrates an inside (wearer-facing side) of the article 100.

Throughout the present disclosure, a reference to a belt type disposable wearable absorbent article can refer to an embodiment that is fastenable or to an embodiment without fasteners. A reference to a belt type disposable wearable absorbent article can also refer to an embodiment of an article with one or more waist and/or leg openings that are preformed (i.e. formed during manufacture of the article) or to an embodiment of an article with waist and leg openings that are not preformed. Thus, each embodiment of a disposable wearable absorbent article of the present disclosure that is described as belt type can be configured in any of these ways, as will be understood by one of ordinary skill in the art.

In FIG. 1A, a longitudinal centerline 113 and a lateral centerline 117 provide lines of reference for referring to relative locations of parts of the article 100. When a first part is nearer to the longitudinal centerline 113 than a second part, the first part can be considered laterally inboard 112 to the second part. Similarly, the second part can be considered laterally outboard 114 from the first part. The first part would be proximal relative to the second part and the second part would be distal relative to the first part. When a third part is nearer to the lateral centerline 117 than a fourth part, the third part can be considered longitudinally inboard 116 to the fourth part. Similarly, the fourth part can be considered longitudinally outboard 118 from the third part. The third part would be proximal relative to the fourth part and the fourth part would be distal relative to the third part. Throughout the present disclosure, when one part is simply referred to as inboard from another part, the one part is laterally inboard and/or longitudinally inboard from the other part. In the same way, when one part is simply referred to as outboard from another part, the one part is laterally outboard and/or longitudinally outboard from the other part.

FIG. 1A includes arrows indicating relative directions for laterally inboard 112, laterally outboard 114, longitudinally inboard 116, and longitudinally outboard 118, with respect to the article 100. Throughout the present disclosure, unless otherwise stated, a reference to a longitudinal dimension, measurement, line, or direction refers to a dimension, measurement, line, or direction substantially or completely parallel to the longitudinal centerline 113, and a reference to a lateral dimension, measurement, line, or direction refers to a dimension, measurement, line, or direction substantially or completely parallel to the lateral centerline 117.

The article 100 includes a front 124 and a back 126. The front 124 is a portion of the article 100 disposed generally proximate to and/or below the belly of a wearer, when the article 100 is worn by the wearer. A reference to the "front" can mean the front itself, part, or parts, or substantially all, or all of an element in the front, and/or a disposition in the front, depending on the context of the reference. The back 126 is a portion of the article 100 disposed generally proximate to and/or below the back of a wearer, when the article 100 is worn by the wearer. A reference to the "back" can mean the back itself, part, or parts, or substantially all, or all of an element in the back, and/or a disposition in the back, depending on the context of the reference. The lateral centerline 117 of the article 100 divides the article longitudinally into halves and forms a boundary between the front 124 and the back 126. The terminology for front and back, described above, is used for disposable wearable absorbent articles throughout the present disclosure, unless otherwise indicated.

The article 100 includes a belt 160 and a center chassis 120. A front belt portion 161 and a back belt portion 169 form the belts 160. The article 100 includes an absorbent core 127 that extends from the front belt portion 161 through the center chassis 120 to the back belt portion. The center chassis 120 includes a topsheet 106 that is inward to the absorbent core 127 and a backsheet 107 that is outward from the absorbent core 127.

The front 124 includes a front belt portion 161 with a front waist area that is adjacent to a front waist edge 109 and is one-third to one-quarter of the overall longitudinal length of the article. The back 126 includes a back belt portion 169 with a back waist area that is adjacent to a back waist edge 104 and is one-third to one-quarter of the overall longitudinal length of the article. The center chassis 120 includes a crotch region disposed between the front waist region and the rear waist region, wherein the crotch region includes the lateral centerline 117. The absorbent core 127 extends from the front 124 to the back 126.

Figure 1C:
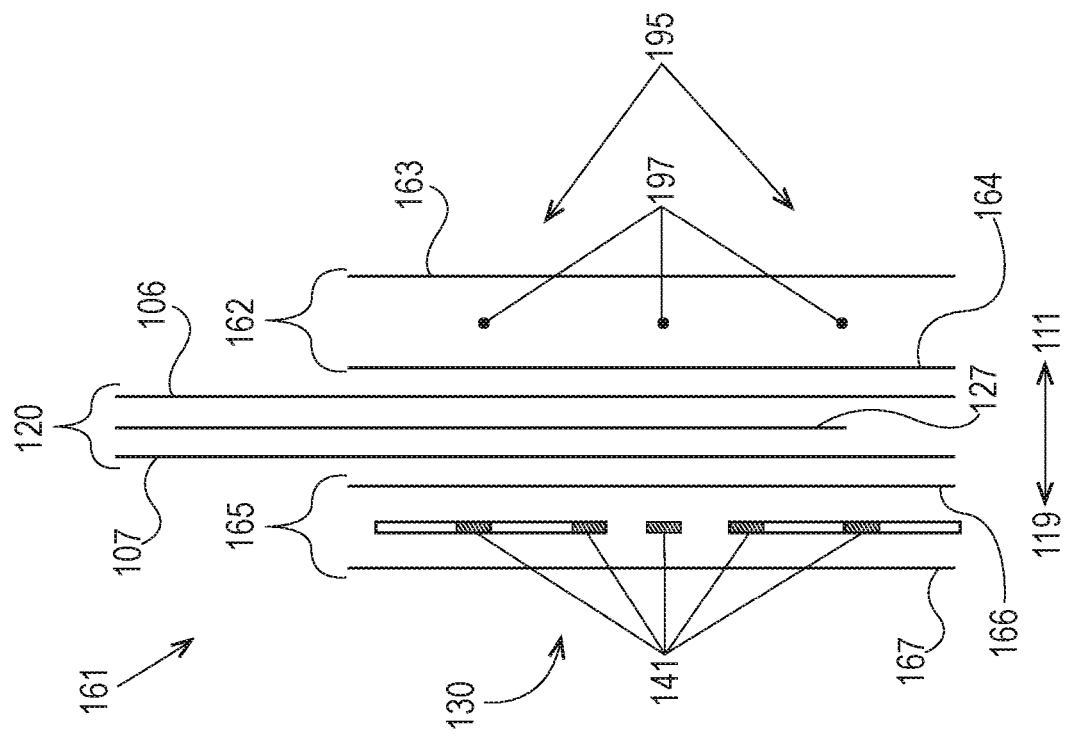
FIG. 1C illustrates an exploded cross-sectional side view of part of the front of the article of FIG. 1A, taken at a second sectional line.
Figure 1B:
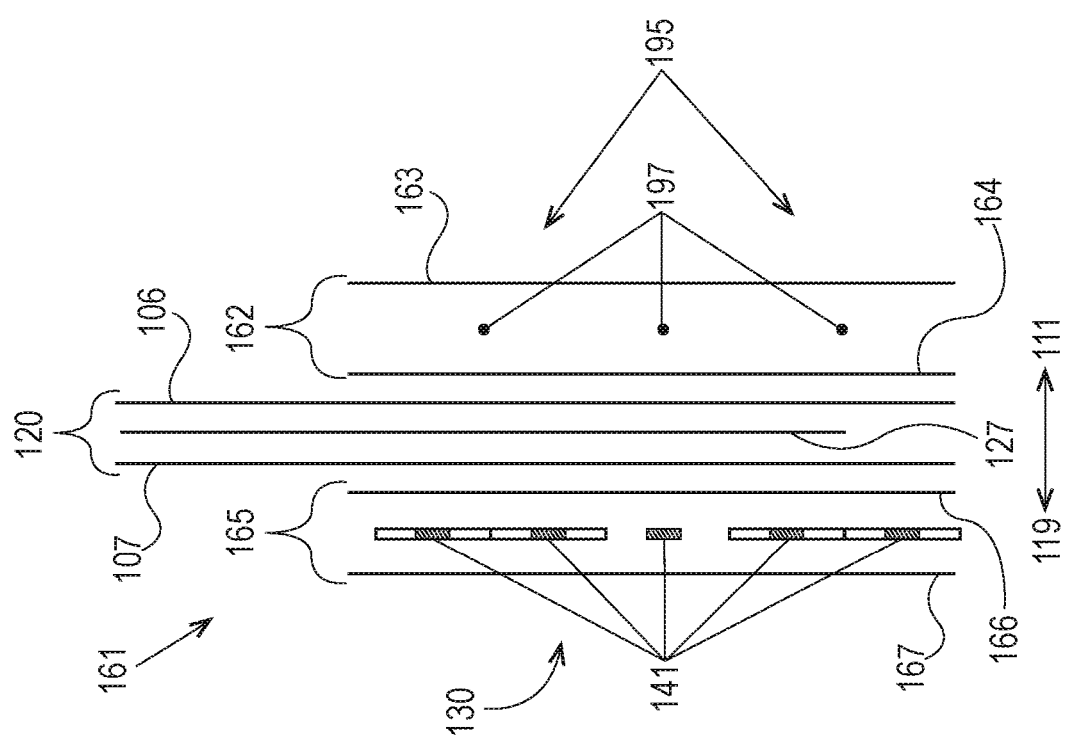
FIG. 1B illustrates an exploded cross-sectional side view of part of the front of the article of FIG. 1A, taken at a first sectional line.

The front belt portion 161 has a front inner belt portion 162 and a front outer belt portion 165, as illustrated in FIGS. 1B and 1C. The front inner belt portion 162 includes a plurality 195 of front shaping elastics 197. The plurality 195 is configured in the same way as the plurality 495 of the embodiment of FIG. 4A. The front outer belt portion 165 includes an anchoring system 130, with anchoring elastics 141. The anchoring elastics 141 of the anchoring system 130 are configured in the same way as the plurality of shaping elastics 895 of the embodiment of FIG. 8B, except that the elastics are anchoring elastics, which work together in the form of a Circumferential Anchoring Member (CAM) as defined and described herein, similar to the front CAM 1141 of the embodiment of FIG. 11B. Together, the plurality 195 of front shaping elastics 197 and the plurality of anchoring elastics 141 form the first embodiment of elastics in multiple layers.

The terms inner and outer as they apply to the inner belt portion and outer belt portion are intended to provide a relative position of the two portions in relationship to each other. In other words, the inner belt portion is positioned closer to the wearer-facing surface of the article than the outer belt portion and the outer belt portion is positioned relatively closer to the garment-facing surface of the article than the inner belt portion. In certain embodiments the inner belt portion may form part of the inner, wearer-facing, surface of the article and the outer belt portion may form part, or all, of the outer, garment-facing, surface of the article. One or both of the inner belt portion and the outer belt portion may be disposed outwardly of the backsheet or alternatively inward of the backsheet.

The inner and/or outer belts may be formed in a variety of shapes. The inner and outer belts may be rectangular or may have inner and outer longitudinally opposed edges that are concave with regard to the waist edge and lateral axis. The shape may also substantially follow the shape or curvature of the elastics disposed in the respective belt structure.

In the embodiment of FIG. 1A, the back belt portion 169 has no elastics. However, in various embodiments, the back belt portion 169 can be configured in the same way as the front belt portion 161 or the back belt portion 169 can have elastics configured in a different way. Moreover, for the embodiment of FIG. 1A, as well as any other embodiment disclosed herein, any configuration of shaping and/or anchoring elastics disclosed in the front or the back of the absorbent article may be combined in part or in whole with any other configuration of elastics disclosed in the other respective end of the absorbent article. In other words, absorbent article embodiments are contemplated herein that are formed from any front belt portion disclosed herein integrated in part or in whole with any back belt portion disclosed herein.

FIG. 1B illustrates an exploded cross-sectional side view of the front belt portion 161 of the article 100 of FIG. 1A, taken at a first sectional line. FIG. 1B includes an inward direction 111 (toward the wearer, and away from the outer garment) and an outward direction 119 (away from the wearer, and toward the outer garment). This terminology for inward, inner, outward, and outer, is used for disposable wearable absorbent articles throughout the present disclosure, unless otherwise indicated.

The front inner belt portion 162 includes an inner belt layer 163, the plurality 195 of front shaping elastics 197, and an outer belt layer 164. The belt inner layer 163 is the innermost belt layer. The plurality 195 of front shaping elastics 197 is outward 119 from the inner belt layer 163. The outer belt layer 164 is outward 119 from the plurality of shaping elastics 197. In various embodiments, the plurality 195 of front shaping elastics 197 can be joined to either or both of the inner belt layer 163 and the outer belt layer 164.

The inner belt layer 163 and/or the outer belt layer 164 can be a nonwoven, a film, a laminate that includes a nonwoven and a film, or any other kind of material suitable for forming a layer of material. In various alternative embodiments, the inner belt layer 163 or the outer belt layer 164 may be omitted. In various alternative embodiments, the front inner belt portion 162 can also include one or more additional materials or layers.

The front outer belt portion 165 includes an inner belt layer 166, the anchoring system 130 formed from the plurality of anchoring elastics 141 and an outer belt layer 167. The plurality of anchoring elastics 141 is outward 119 from the inner belt layer 166. The outer belt layer of material 167 is outward 119 from the plurality of anchoring elastics 141. The outer layer 167 is the outermost layer of the belt portion 165. In various embodiments, the plurality of anchoring elastics 141 can be joined to either or both of the inner belt layer 166 and the outer belt layer 167. The inner belt layer 166 and/or the outer belt layer 167 can be a nonwoven, a film, a laminate that includes a nonwoven and a film, or any other kind of material suitable for forming a layer of material. In various alternative embodiments, the inner belt layer 166 or the outer belt layer 167 may be omitted. In various alternative embodiments, the front outer belt portion 165 can also include one or more additional materials or layers.

The shaping elastics 197 and the anchoring elastics 141 are separated into multiple layers. Since the shaping elastics are separated from the anchoring elastics, they can function somewhat independently of each other. The shaping elastics can at least assist in providing conforming fit and distributing contact forces over the wearer's skin while the anchoring elastics can at least assist in holding the article in place on the wearer. As a result, embodiments of the belt type disposable wearable absorbent article 100 can feel comfortable, look attractive, and perform well while being worn.

In the embodiment of FIG. 1B, the center chassis 120 is outward 119 from the front inner belt portion 162, and the front outer belt portion 165 is outward 119 from the center chassis 120. However, in an alternative embodiment, the front outer belt portion 165 can be disposed outward 119 from front inner belt portion 162 and inward 111 to the center chassis 120. In another alternative embodiment, the front inner belt portion 162 can be disposed outward 119 from the center chassis 120 and inward to the front outer belt portion 165. In these alternative embodiments, the outer belt layer 164 can be joined to the inner belt layer 166, or these two layers of material can even be substituted with a single layer of material.

FIG. 1C illustrates an exploded cross-sectional view of the front belt portion 161 of the article 100 of FIG. 1A, taken at a second sectional line.

Figure 1D:
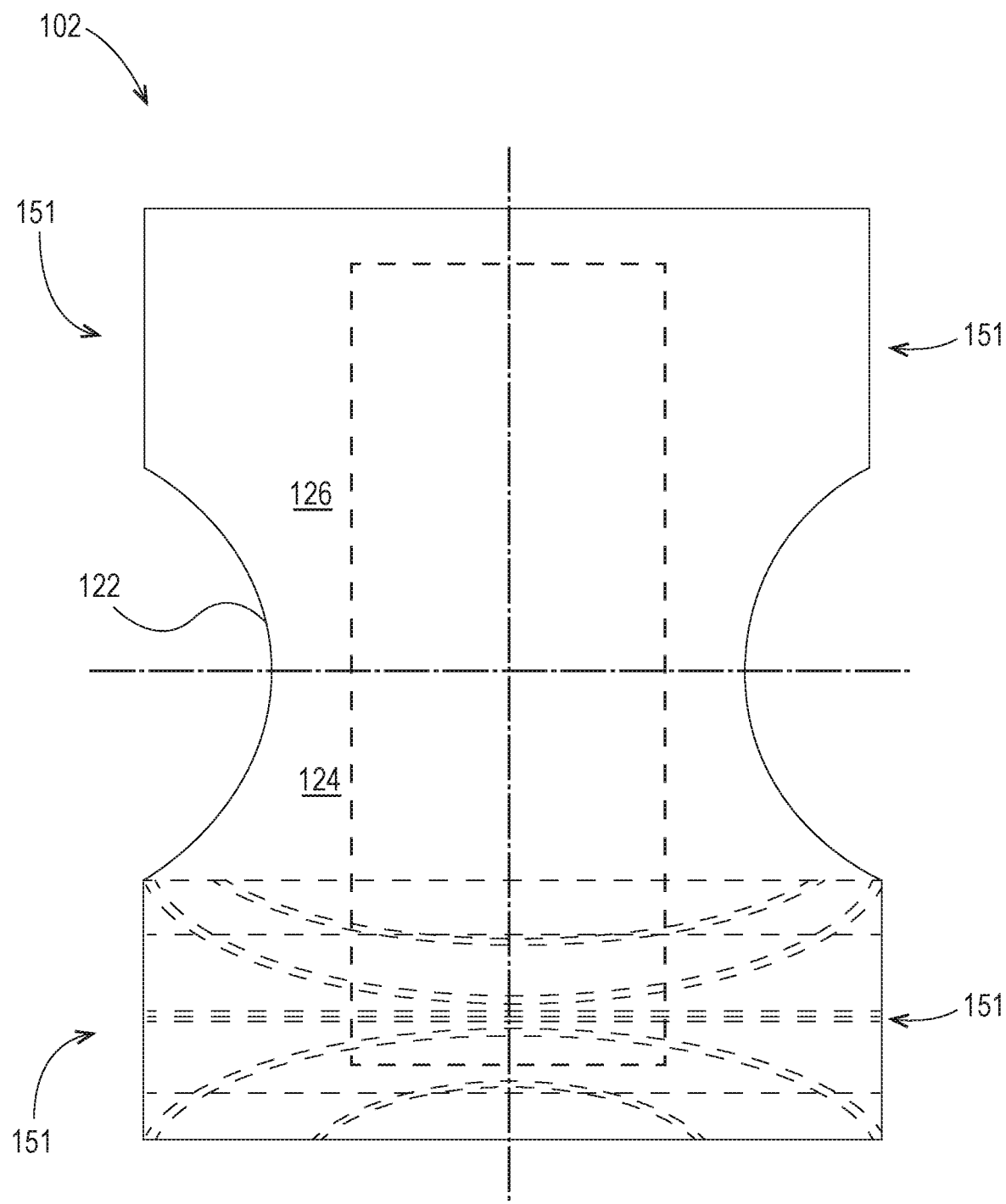
FIG. 1D illustrates a plan view of a pant type disposable wearable absorbent article, which includes the first embodiment of elastics in multiple layers.

FIG. 1D illustrates a plan view of a pant type disposable wearable absorbent article 102, which includes the first embodiment of elastics in multiple layers. The first embodiment of elastics in the pant type article 102 of FIG. 1D is configured in the same way as the first embodiment of elastics in the belt type article 100 of FIG. 1A, except for differences in type of chassis.

Throughout the present disclosure, a reference to a pant type disposable wearable absorbent article can refer to an embodiment that is fastenable or to an embodiment without fasteners. A reference to a pant type disposable wearable absorbent article can also refer to an embodiment of an article with one or more waist and/or leg openings that are preformed (i.e. formed during manufacture of the article) or to an embodiment of an article with waist and leg openings that are not preformed. Thus, each embodiment of a disposable wearable absorbent article of the present disclosure that is described as pant type can be configured in any of these ways, as will be understood by one of ordinary skill in the art.

The article 102 includes a pant type chassis 122 with a front 124 and a back 126. The article 102 also includes side panels 151. When the article 102 is formed for wearing, each front side panel 151 is connected to a corresponding back side panel 151 at a side panel connection.

Since the pant type disposable wearable absorbent article 102 has the first embodiment of elastics, with shaping elastics and anchoring elastics separated into multiple layers, these elastics can function somewhat independently of each other, and the article 102 can feel comfortable, look attractive, and perform well while being worn.

Figure 1E:
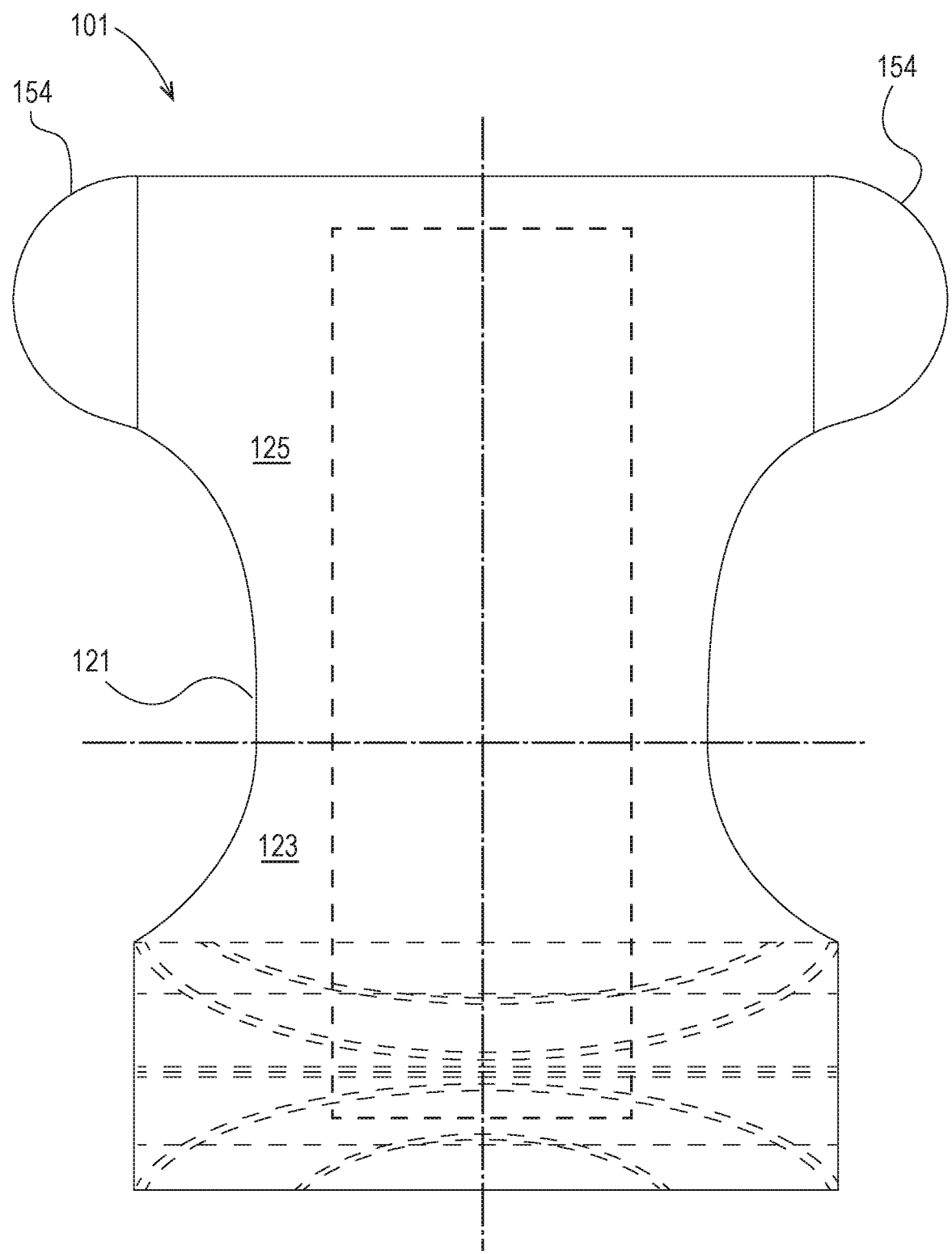
FIG. 1E illustrates a plan view of a front fastenable disposable wearable absorbent article, which includes the first embodiment of elastics in multiple layers.

FIG. 1E illustrates a plan view of a front fastenable disposable wearable absorbent article 101, which includes the first embodiment of elastics in multiple layers. The first embodiment of elastics in the front fastenable article 101 of FIG. 1E is configured in the same way as the first embodiment of elastics in the belt type article 100 of FIG. 1A, except for differences in type of chassis.

The article 101 includes a front fastenable chassis 121 with a front 123 and a back 125. The article 101 also includes fasteners 154 in the back 125. When the article 102 is formed for wearing, each of the fasteners 154 in the back 125 connects to a portion of the front 123 to form a fastening connection.

While the present disclosure refers to front fastenable disposable wearable absorbent articles, the present disclosure also contemplates alternate embodiments of disposable wearable absorbent articles, as described herein, wherein the disposable wearable absorbent articles are rear-fastenable or side-fastenable or belt-fastenable. Thus, each embodiment of a disposable wearable absorbent article of the present disclosure that is described as front fastenable can also be configured in any of these ways, as will be understood by one of ordinary skill in the art. Useful fasteners may include tape tabs, hook-and-loop fasteners, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526.

Since the front fastenable disposable wearable absorbent article 101 has the first embodiment of elastics, with shaping elastics and anchoring elastics separated into multiple layers, these elastics can function somewhat independently of each other, and the article 101 can feel comfortable, look attractive, and perform well while being worn.

Figure 2A:
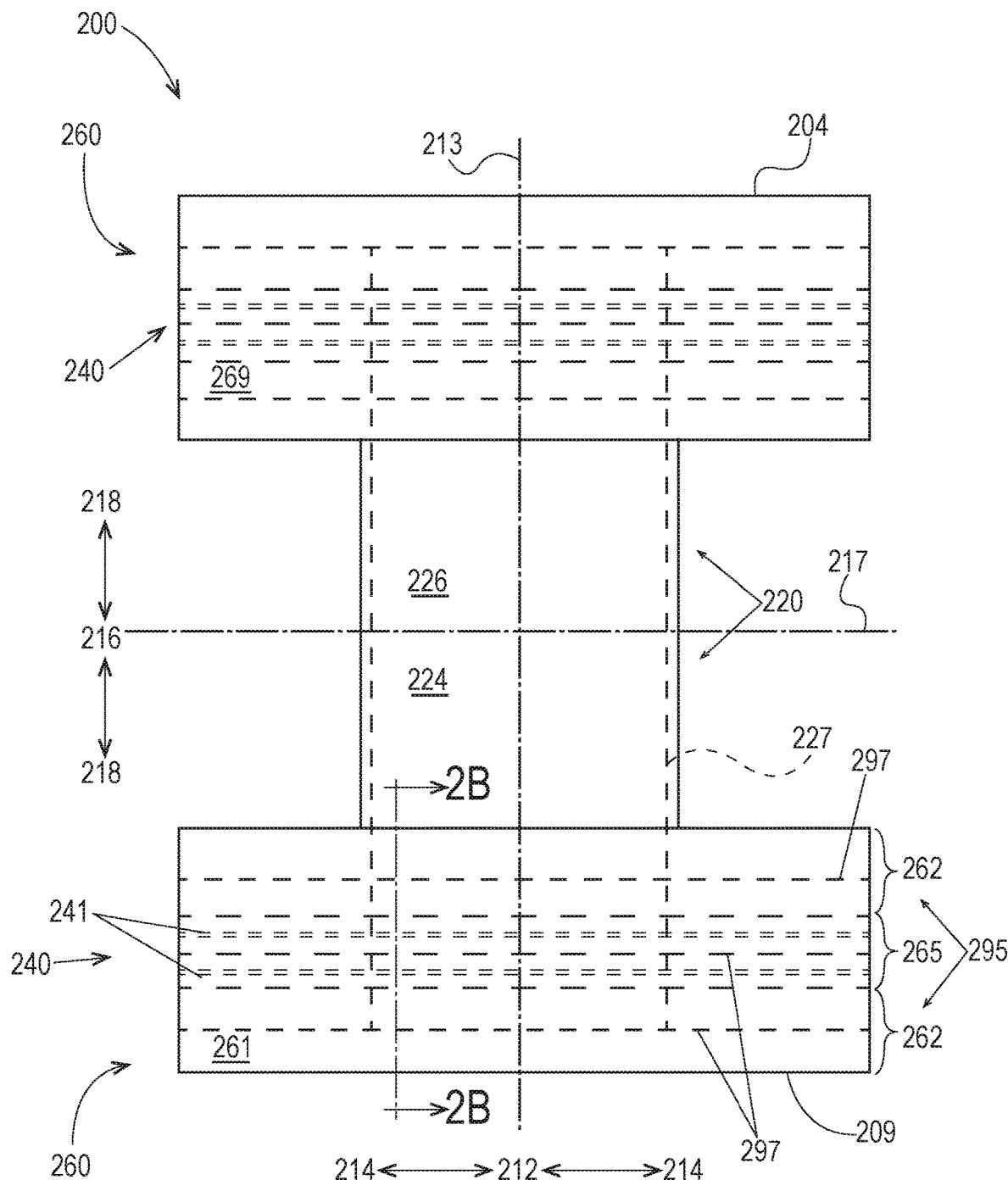
FIG. 2A illustrates a plan view of a belt type disposable wearable absorbent article, which includes a second embodiment of elastics in multiple layers.

FIG. 2A illustrates a plan view of a belt type disposable wearable absorbent article 200, which includes a second embodiment of elastics in multiple layers. FIG. 2A illustrates a plan view of a belt type disposable wearable absorbent article 200. The view of FIG. 2A illustrates an inside (wearer-facing side) of the article 200.

In FIG. 2A, a longitudinal centerline 213 and a lateral centerline 217 provide lines of reference for referring to relative locations of parts of the article 200. FIG. 2A includes arrows indicating relative directions for laterally inboard 212, laterally outboard 214, longitudinally inboard 216, and longitudinally outboard 218, with respect to the article 200.

The article 200 includes a front 224 and a back 226. The article 200 includes a belt 260 and a center chassis 220. A front belt portion 261 and a back belt portion 269 form the belt 260. The article 200 includes an absorbent core 227 that extends from the front belt portion 261 through the center chassis 220 to the back belt portion 269. The center chassis 220 includes a topsheet 206 that is inward from the absorbent core 227 and a backsheet 207 that is outward from the absorbent core 227.

The front 224 includes a front belt portion 261 with a front waist area that is adjacent to a front waist edge 209 and is one-third to one-quarter of the overall longitudinal length of the article. The back 226 includes a back belt portion 269 with a back waist area that is adjacent to a back waist edge 204 and is one-third to one-quarter of the overall longitudinal length of the article. The center chassis 220 includes a crotch region disposed between the front waist region and the rear waist region, wherein the crotch region includes the lateral centerline 217. The absorbent core 227 extends from the front 224 to the back 226.

Figure 2B:
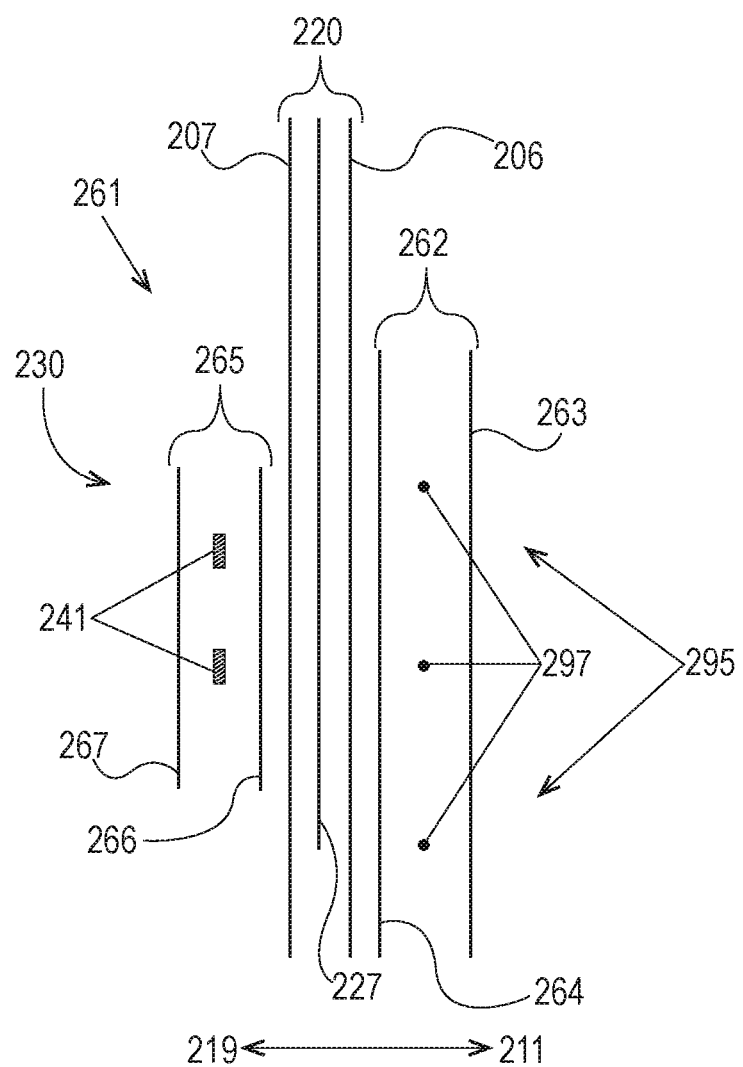
FIG. 2B illustrates an exploded cross-sectional side view of part of the front of the article of FIG. 2A, taken at a sectional line.

The front belt portion 261 has a front inner belt portion 262 and a front outer belt portion 265, as illustrated in FIG. 2B. The front inner belt portion 262 includes a plurality 295 of front shaping elastics 297 (e.g., the first plurality of elastics). The plurality 295 is configured in the same way as the plurality 495 of the embodiment of FIG. 4A. The front outer belt portion 265 includes an anchoring system 230, with anchoring elastics 241 (e.g., the second plurality of elastics). The anchoring elastics 241 of the anchoring system 230 form a CAM, similar to the front CAM 1141 of the embodiment of FIG. 11B. Together, the plurality 295 of front shaping elastics 297 and the plurality of anchoring elastics 241 form the second embodiment of elastics in multiple layers.

For embodiments comprising pluralities of elastics in only one of the front and back waist regions, and in the inner belt portions and outer belt portions, the plurality of elastics disposed in the inner belt portion in the waist region is referred to hereinafter as the first plurality of elastics. The plurality of elastics disposed in the outer belt portion in the waist region is referred to hereinafter as the second plurality of elastics.

For embodiments comprising pluralities of elastics in both front and back waist regions, and in the inner belt portions and outer belt portions, the plurality of elastics disposed in the inner belt portion in the front waist region is referred to hereinafter as the first plurality of elastics. The plurality of elastics disposed in the outer belt portion in the front waist region is referred to hereinafter as the second plurality of elastics. The plurality of elastics disposed in the inner belt portion in the back waist region is referred to hereinafter as the third plurality of elastics. The plurality of elastics disposed in the outer belt portion in the back waist region is referred to hereinafter as the fourth plurality of elastics.

In the embodiment of FIG. 2A, the back belt portion 269 is configured in the same way as the front belt portion 261. However, in various embodiments, the back belt portion 269 can have elastics configured in a different way or can be configured with no elastics.

FIG. 2B illustrates an exploded cross-sectional side view of the front belt portion 261 of the article 200 of FIG. 2A, taken at a first sectional line. FIG. 2B includes an inward direction 211 and an outward direction 219.

The front inner belt portion 262 includes an inner belt layer 263, the plurality 295 of front shaping elastics 297, and an outer belt layer 264. The inner belt layer 263 is the innermost layer. The plurality 295 of front shaping elastics 297 is outward 219 from the inner belt layer 263. The outer belt layer 264 is outward 219 from the plurality of shaping elastics 297. In various embodiments, the plurality 295 of front shaping elastics 297 can be joined to either or both of the inner belt layer 263 and the outer belt layer 264.

The inner belt layer 263 and/or the outer belt layer 264 can be a nonwoven, a film, a laminate that includes a nonwoven and a film, or any other kind of material suitable for forming a layer of material. In various alternative embodiments, the inner belt layer 263 or the outer belt layer 264 may be omitted. In various alternative embodiments, the front inner belt portion 262 can also include one or more additional materials or layers.

The front outer belt portion 265 includes an inner belt layer 266, the anchoring system 230 formed from the plurality of anchoring elastics 241, and an outer belt layer 267. The plurality of anchoring elastics 241 is outward 219 from the inner belt layer 266. The outer belt layer 267 is outward 219 from the plurality of anchoring elastics 241. The outer belt layer 267 is the outermost layer. In various embodiments, the plurality of anchoring elastics 241 can be joined to either or both of the inner belt layer 266 and the outer belt layer 267.

The inner belt layer 266 and/or the outer belt layer 267 can be a nonwoven, a film, a laminate that includes a nonwoven and a film, or any other kind of material suitable for forming a layer of material. In various alternative embodiments, the inner belt layer 266 or the outer belt layer 267 may be omitted. In various alternative embodiments, the front outer belt portion 265 can also include one or more additional materials or layers.

The shaping elastics 297 and the anchoring elastics 241 are separated into multiple layers. Since the shaping elastics are separated from the anchoring elastics, they can function somewhat independently of each other. The shaping elastics can at least assist in providing conforming fit and distributing contact forces over the wearer's skin while the anchoring elastics can at least assist in holding the article in place on the wearer. As a result, embodiments of the belt type disposable wearable absorbent article 200 can feel comfortable, look attractive, and perform well while being worn.

In the embodiment of FIG. 2B, the center chassis 220 is outward 219 from the front inner belt portion 262, and the front outer belt portion 265 is outward 219 from the center chassis. However, in an alternative embodiment, the front outer belt portion 265 can be disposed outward 219 from front inner belt portion 262 and inward 211 to the center chassis 220. In another alternative embodiment, the front inner belt portion 262 can be disposed outward 219 from the center chassis 220 and inward to the front outer belt portion 265. In these alternative embodiments, the outer belt layer 264 can be joined to the inner belt layer 266, or these two layers of material can even be substituted with a single layer of material.

Figure 2C:
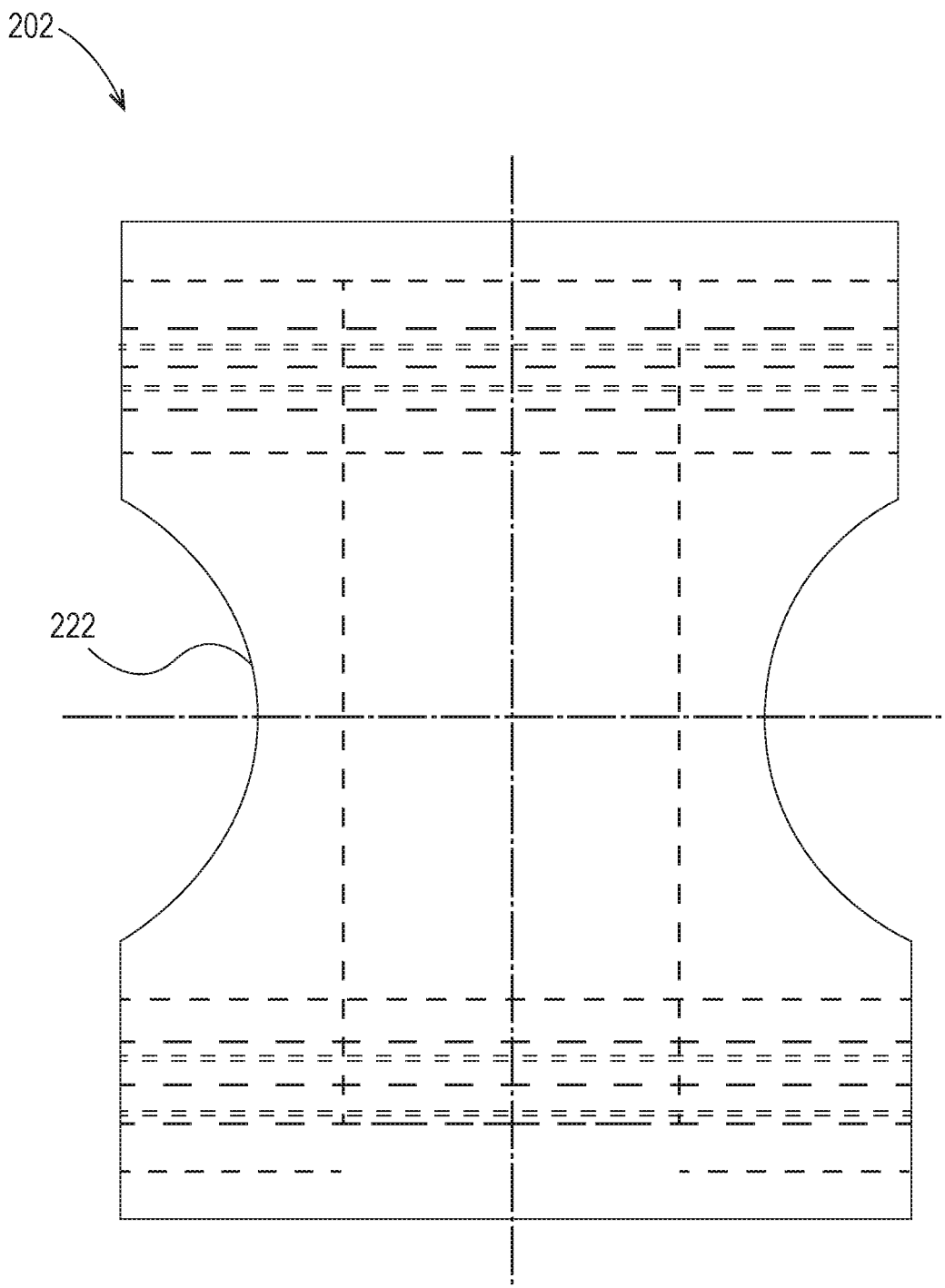
FIG. 2C illustrates a plan view of a pant type disposable wearable absorbent article, which includes the second embodiment of elastics in multiple layers.

FIG. 2C illustrates a plan view of a pant type disposable wearable absorbent article 202, which includes the second embodiment of elastics in multiple layers. The second embodiment of elastics in the pant type article 202 of FIG. 2C is configured in the same way as the second embodiment of elastics in the belt type article 200 of FIG. 2A, except for differences in type of chassis. The article 202 includes a pant type chassis 222. Since the pant type disposable wearable absorbent article 202 has the second embodiment of elastics, with shaping elastics and anchoring elastics separated into multiple layers, these elastics can function somewhat independently of each other, and the article 202 can feel comfortable, look attractive, and perform well while being worn.

Figure 2D:
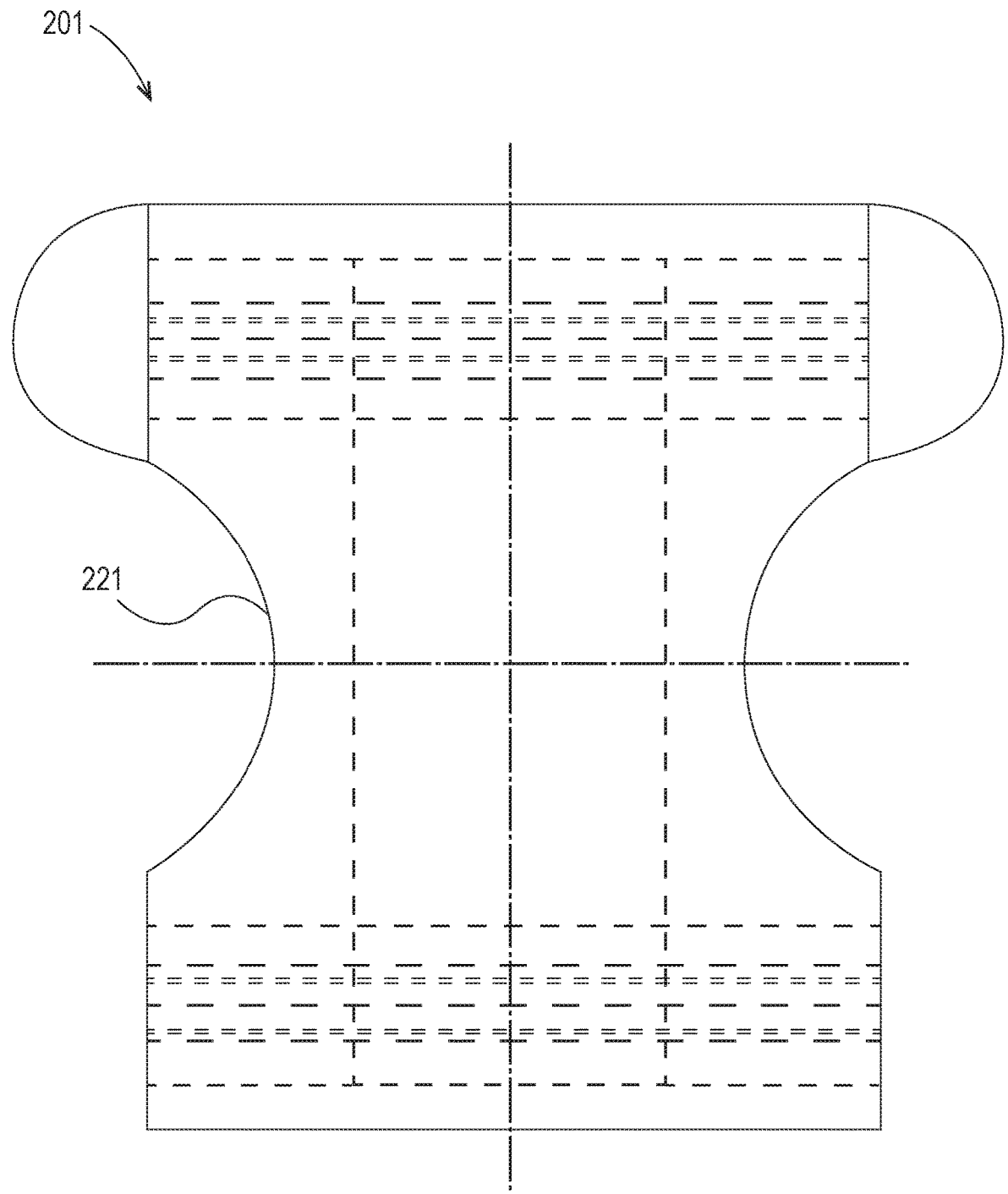
FIG. 2D illustrates a plan view of a front fastenable disposable wearable absorbent article, which includes the second embodiment of elastics in multiple layers.

FIG. 2D illustrates a plan view of a front/side fastenable disposable wearable absorbent article 201, which includes the second embodiment of elastics in multiple layers. The second embodiment of elastics in the front/side fastenable article 201 of FIG. 2D is configured in the same way as the second embodiment of elastics in the belt type article 200 of FIG. 2A, except for differences in type of chassis. The article 201 includes a front/side fastenable chassis 221. Since the front/side fastenable disposable wearable absorbent article 201 has the second embodiment of elastics, with shaping elastics and anchoring elastics separated into multiple layers, these elastics can function somewhat independently of each other, and the article 201 can feel comfortable, look attractive, and perform well while being worn. In certain embodiments the anchoring elastics can be positioned in line with the fastener such that the fasteners provide a defined connection between the front and back of the article thereby linking the anchoring elastics in one waist region with the anchoring elastics in the opposing waist region.

Figure 3A:
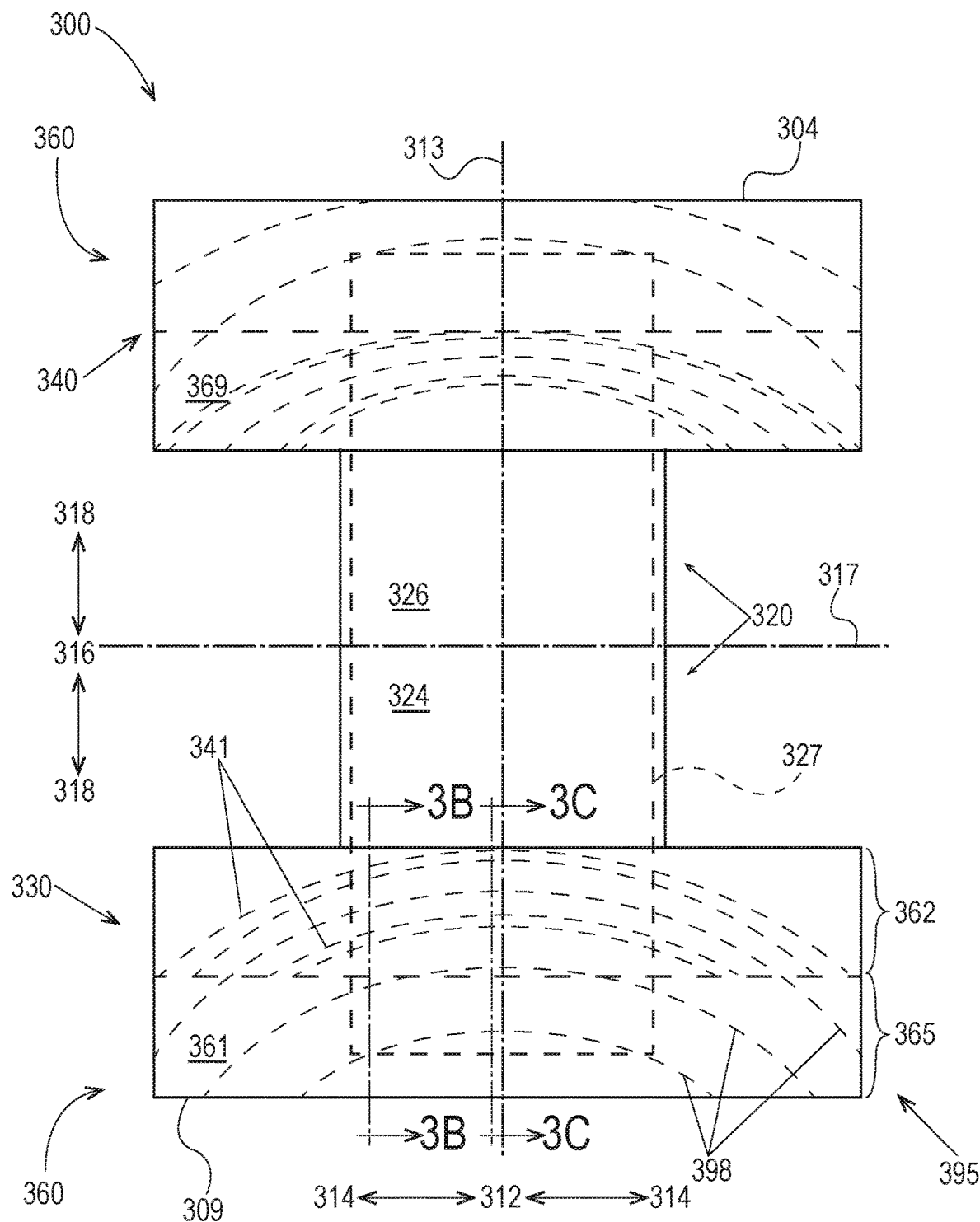
FIG. 3A illustrates a plan view of a belt type disposable wearable absorbent article, which includes a third embodiment of elastics in multiple layers.

FIG. 3A illustrates a plan view of a belt type disposable wearable absorbent article 300, which includes a third embodiment of elastics in multiple layers. FIG. 3A illustrates a plan view of a belt type disposable wearable absorbent article 300. The view of FIG. 3A illustrates an inside (wearer-facing side) of the article 300.

In FIG. 3A, a longitudinal centerline 313 and a lateral centerline 317 provide lines of reference for referring to relative locations of parts of the article 300. FIG. 3A includes arrows indicating relative directions for laterally inboard 312, laterally outboard 314, longitudinally inboard 316, and longitudinally outboard 318, with respect to the article 300.

The article 300 includes a front 324 and a back 326. The article 300 includes a belt 360 and a center chassis 320. A front belt portion 361 and a back belt portion 369 form the belt 360. The article 300 includes an absorbent core 327 that extends from the front belt portion 361 through the center chassis 320 to the back belt portion 369. The center chassis 320 includes a topsheet 306 that is inward of the absorbent core 327 and a backsheet 307 that is outward of the absorbent core 327.

The front 324 includes a front belt portion 361 with a front waist area that is adjacent to a front waist edge 309 and is one-third to one-quarter of the overall longitudinal length of the article. The back 326 includes a back belt portion 369 with a back waist area that is adjacent to a back waist edge 304 and is one-third to one-quarter of the overall longitudinal length of the article. The center chassis 320 includes a crotch region disposed between the front waist region and the rear waist region, wherein the crotch region includes the lateral centerline 317. The absorbent core 327 extends from the front 324 into the back 326.

The front belt portion 361 has a front inner belt portion 362 and a front outer belt portion 365, as illustrated in FIGS. 3B and 3C. The front inner belt portion 362 includes a plurality 395 of front shaping elastics 398. The plurality 395 is configured in the same way as the plurality 695 of the embodiment of FIG. 6A. The front outer belt portion 365 includes an anchoring system 330, with anchoring elastics 341. The anchoring elastics 341 of the anchoring system 330 are configured in the same way as the plurality of shaping elastics 695 of the embodiment of FIG. 6A, except that the elastics are anchoring elastics, which work together in the form of a CAM, similar to the front CAM 1141 of the embodiment of FIG. 11B. Together, the plurality 395 of front shaping elastics 398 and the plurality of anchoring elastics 341 form the third embodiment of elastics in multiple layers.

In the embodiment of FIG. 3A, the back belt portion 369 also has elastics. The back belt portion 369 has a plurality of front shaping elastics configured in the same way as the plurality 591 of the embodiment of FIG. 5A, and an anchoring system, with anchoring elastics configured in the same way as the plurality of shaping elastics 591 of the embodiment of FIG. 5A, except that the elastics are anchoring elastics, which work together in the form of a CAM, similar to the front CAM 1141 of the embodiment of FIG. 11B. Together, the plurality of front shaping elastics and the plurality of anchoring elastics in the back belt portion form an embodiment of elastics in multiple layers. In various embodiments, the back belt portion 369 can be configured in the same way as the front belt portion 361, or the back belt portion 369 can have elastics configured in a different way, or the back belt portion 369 can be configured without elastics.

FIG. 3A illustrates an embodiment that has elastics in the front belt portion that are convex to the lateral centerline on the center chassis, and elastics in the back belt portion that are concave to the lateral centerline on the center chassis. When these elastics are integrated together in an absorbent article, such absorbent article (when donned on a wearer) has a sustained dynamic fit to improve containment of body exudates and wearer comfort/mobility. The elastics form a continuum of anchoring that extends from the small of users back, to below the nave at the belly crease, and back to the small of the back. Thus, this elastic continuum follows the minimum circumference of the anatomy and provides the greatest level of anchoring.

FIG. 3B illustrates an exploded cross-sectional side view of the front belt portion 361 of the article 300 of FIG. 3A, taken at a first sectional line. FIG. 3B includes an inward direction 311 and an outward direction 319.

The front inner belt portion 362 includes an inner belt layer 363, the plurality 395 of front shaping elastics 398, and an outer belt layer 364. The inner belt layer 363 is the innermost layer. The plurality 395 of front shaping elastics 398 is outward 319 from the inner belt layer 363. The outer belt layer 364 is outward 319 from the plurality of shaping elastics 398. In various embodiments, the plurality 395 of front shaping elastics 398 can be joined to either or both of the inner belt layer 363 and the outer belt layer 364.

The inner belt layer 363 and/or the outer belt layer 364 can be a nonwoven, a film, a laminate that includes a nonwoven and a film, or any other kind of material suitable for forming a layer of material. In various alternative embodiments, the inner belt layer 363 or the outer belt layer 364 may be omitted. In various alternative embodiments, the front inner belt portion 362 can also include one or more additional materials or layers.

The front outer belt portion 365 includes an inner belt layer 366, the anchoring system 330 formed from the plurality of anchoring elastics 341, and an outer belt layer 367. The plurality of anchoring elastics 341 is outward 319 from the inner belt layer 366. The outer belt layer 367 is outward 319 from the plurality of anchoring elastics 341. The outer belt layer 367 is the outermost layer. In various embodiments, the plurality of anchoring elastics 341 can be joined to either or both of the inner belt layer 366 and the outer belt layer 367.

The inner belt layer 366 and/or the outer belt layer 367 can be a nonwoven, a film, a laminate that includes a nonwoven and a film, or any other kind of material suitable for forming a layer of material. In various alternative embodiments, the inner belt layer 366 or the outer belt layer 367 may be omitted. In various alternative embodiments, the front outer belt portion 365 can also include one or more additional materials or layers.

The shaping elastics 398 and the anchoring elastics 341 are separated into multiple layers. Since the shaping elastics are separated from the anchoring elastics, they can function somewhat independently of each other. The shaping elastics can at least assist in providing conforming fit and distributing contact forces over the wearer's skin while the anchoring elastics can at least assist in holding the article in place on the wearer. As a result, embodiments of the belt type disposable wearable absorbent article 300 can feel comfortable, look attractive, and perform well while being worn.

In the embodiment of FIG. 3B, the center chassis 320 is outward 319 from the front inner belt portion 362, and the front outer belt portion 365 is outward 319 from the center chassis. However, in an alternative embodiment, the front outer belt portion 365 can be disposed outward 319 from front inner belt portion 362 and inward 311 to the center chassis 320. In another alternative embodiment, the front inner belt portion 362 can be disposed outward 319 from the center chassis 320 and inward to the front outer belt portion 365. In these alternative embodiments, the outer belt layer 364 can be joined to the inner belt layer 366, or these two layers of material can even be substituted with a single layer of material.

FIG. 3C illustrates an exploded cross-sectional view of the front belt portion 361 of the article 300 of FIG. 3A, taken at a second sectional line.

Figure 3D:
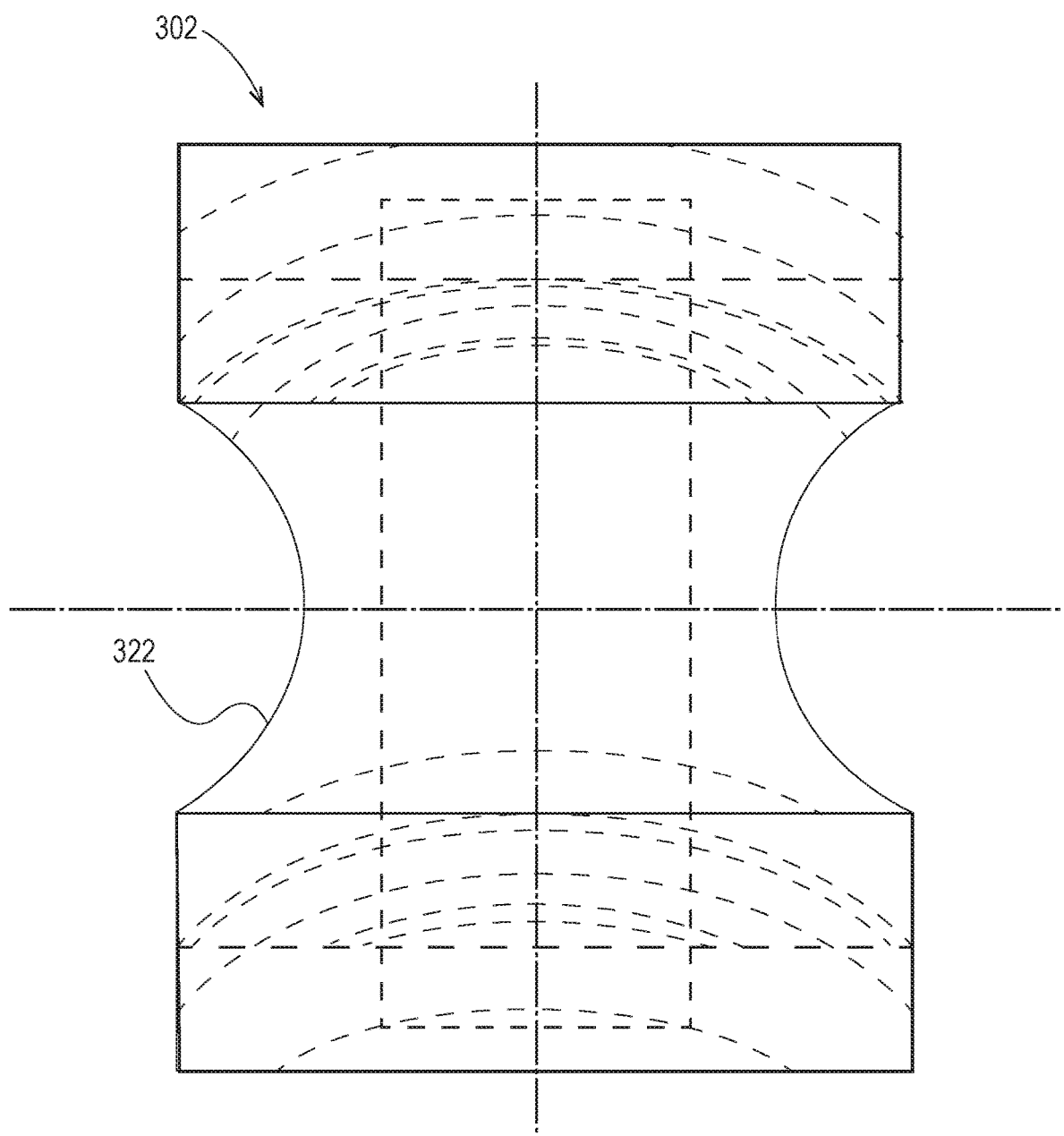
FIG. 3D illustrates a plan view of a pant type disposable wearable absorbent article, which includes the third embodiment of elastics in multiple layers.

FIG. 3D illustrates a plan view of a pant type disposable wearable absorbent article 302, which includes the third embodiment of elastics in multiple layers. The third embodiment of elastics in the pant type article 302 of FIG. 3D is configured in the same way as the third embodiment of elastics in the belt type article 300 of FIG. 3A, except for differences in type of chassis. The article 302 includes a pant type chassis 322. Since the pant type disposable wearable absorbent article 302 has the third embodiment of elastics, with shaping elastics and anchoring elastics separated into multiple layers, these elastics can function somewhat independently of each other, and the article 302 can feel comfortable, look attractive, and perform well while being worn.

Figure 3E:
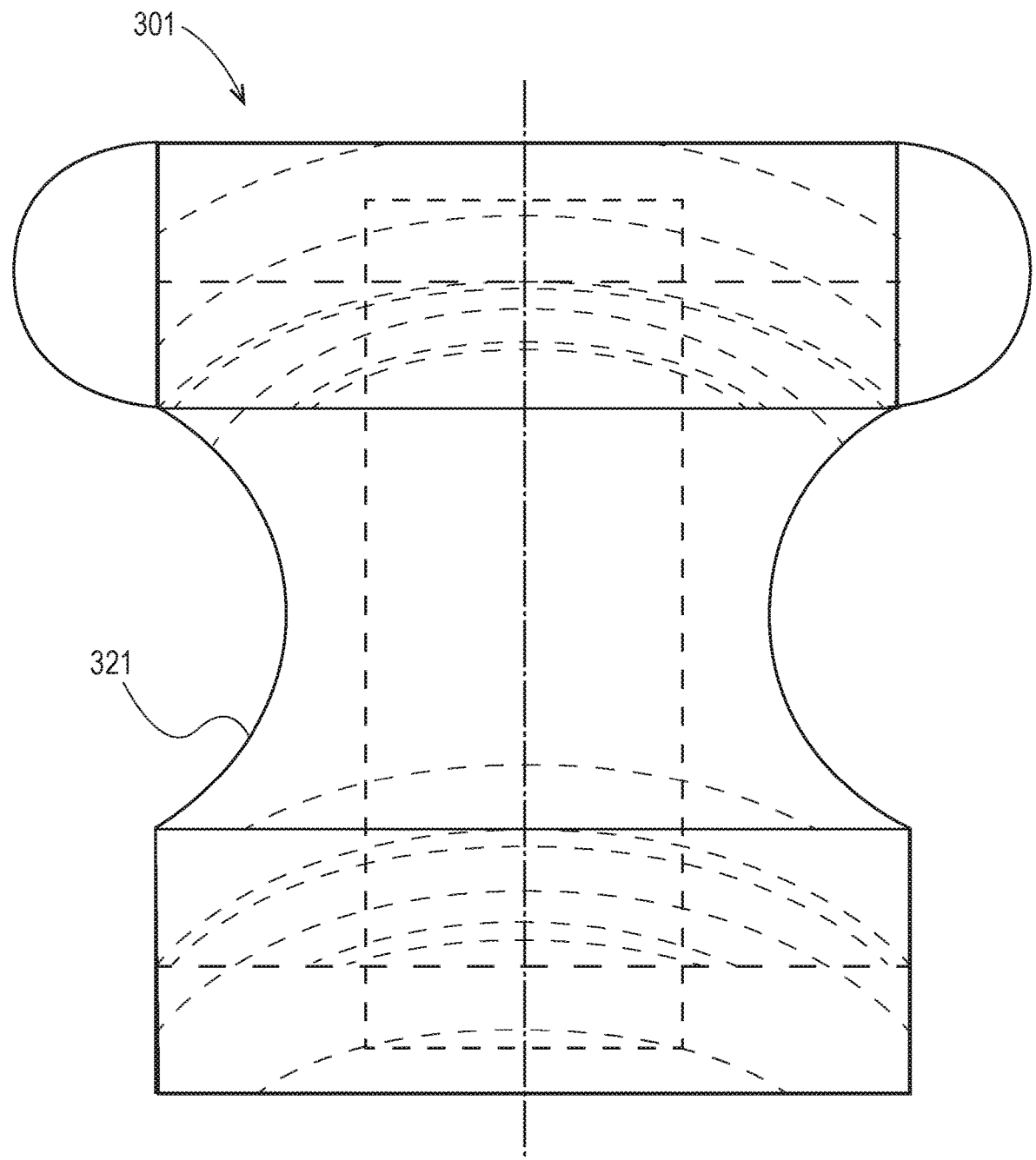
FIG. 3E illustrates a plan view of a front fastenable disposable wearable absorbent article, which includes the third embodiment of elastics in multiple layers.

FIG. 3E illustrates a plan view of a front/side fastenable disposable wearable absorbent article 301, which includes the third embodiment of elastics in multiple layers. The third embodiment of elastics in the front/side fastenable article 301 of FIG. 3E is configured in the same way as the third embodiment of elastics in the belt type article 300 of FIG. 3A, except for differences in type of chassis. Since the front/side fastenable disposable wearable absorbent article 301 has the third embodiment of elastics, with shaping elastics and anchoring elastics separated into multiple layers, these elastics can function somewhat independently of each other, and the article 301 can feel comfortable, look attractive, and perform well while being worn.

The embodiments of FIGS. 4A through 8B describe various pluralities of shaping elastics for use in disposable wearable absorbent articles. These pluralities can be configured in various ways. Shaping elastics can be formed from various materials, such as Lycra, rubber, Spandex, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, rubbers, similar materials, other elastic materials known in the art, and combinations thereof. In some embodiments, shaping elastics can be extruded strand elastics with any number of strands (or filaments). Shaping elastics can have a decitex ranging from 50 to 500, or any integer value for any decitex value in this range, or any range formed by any of these integer values. In FIGS. 4A through 8B, for the purpose of clarity, some underlying parts of the disposable wearable absorbent articles are not shown with hidden lines, so as not to obscure the elastics.

In FIGS. 4A through 8B, for ease of illustration, each plurality of shaping elastics is shown with an exemplary number of elastics. However, each of these pluralities can include any number of elastics. In various alternate embodiments, any of these shaping elastics can be configured in any manner described herein. Each of the pluralities of shaping elastics, of FIGS. 4A through 8B can be configured in a disposable wearable absorbent article to provide a conforming fit and to distribute contact forces over the wearer's skin.

The embodiments of FIGS. 9A through 11B describe various anchoring systems for use in disposable wearable absorbent articles. These anchoring systems can be configured with one or more Circumferential Anchoring Members (CAMs), anchoring bands, Load Distribution Elements (LDEs), spines, and/or other anchoring pathways, in various ways, as described herein. In FIGS. 9A through 11B, for the purpose of clarity, some parts of the disposable wearable absorbent articles are illustrated as transparent, to show structures and features, which might otherwise be hidden by overlying material.

The front of one or more of any of the articles of FIGS. 4A, 5A, 6A, 7A, 8A, 9A, 10A, and 11A when configured to represent a front/side fastenable disposable wearable absorbent article (including any alternative embodiments), can be combined with the back of one or more of any of the articles of FIGS. 4A, 5A, 6A, 7A, 8A, 9A, 10A, and 11A when configured to represent a front/side fastenable disposable wearable absorbent article (including any alternative embodiments). In such combinations, the resulting article can have elastics in multiple layers in the front, the back or both. For front/side fastenable disposable wearable absorbent articles, any front disclosed herein can be combined with any back disclosed herein or known in the art (including any back without elastics), to form further alternative embodiments.

The back of one or more of any of the articles of FIGS. 4A, 5A, 6A, 7A, 8A, 9A, 10A, and 11A when configured to represent a front/side fastenable disposable wearable absorbent article (including any alternative embodiments), can be combined with the front of one or more of any of the articles of FIGS. 4A, 5A, 6A, 7A, 8A, 9A, 10A, and 11A when configured to represent a front/side fastenable disposable wearable absorbent article (including any alternative embodiments). In such combinations, the resulting article can have elastics in multiple layers in the back, the front or both. For front/side fastenable disposable wearable absorbent articles, any back disclosed herein can be combined with any front disclosed herein or known in the art (including any front without elastics), to form further alternative embodiments. In various alternate embodiments, any front/side fastenable disposable wearable absorbent article disclosed herein can be modified to be a belt type article, configured in any way disclosed herein or known in the art.

The front of one or more of any of the articles of FIGS. 4B, 5B, 6B, 7B, 8B, 9B, 10B, and 11B when configured to represent a pant type disposable wearable absorbent article (including any alternative embodiments), can be combined with the back of one or more of any of the articles of FIGS. 4B, 5B, 6B, 7B, 8B, 9B, 10B, and 11B when configured to represent a pant type disposable wearable absorbent article (including any alternative embodiments). In such combinations, the resulting article can have elastics in multiple layers in the front, the back or both. For pant type disposable wearable absorbent articles, any front disclosed herein can be combined with any back disclosed herein or known in the art (including any back without elastics), to form further alternative embodiments.

The back of one or more of any of the articles of FIGS. 4B, 5B, 6B, 7B, 8B, 9B, 10B, and 11B when configured to represent a pant type disposable wearable absorbent article (including any alternative embodiments), can be combined with the front of one or more of any of the articles of FIGS. 4B, 5B, 6B, 7B, 8B, 9B, 10B, and 11B when configured to represent a pant type disposable wearable absorbent article (including any alternative embodiments). In such combinations, the resulting article can have elastics in multiple layers in the back, the front or both. For pant type disposable wearable absorbent articles, any back disclosed herein can be combined with any front disclosed herein or known in the art (including any front without elastics), to form further alternative embodiments. In various alternate embodiments, any pant type disposable wearable absorbent article disclosed herein can be modified to be a belt type article, configured in any way disclosed herein or known in the art.

Figure 4A:
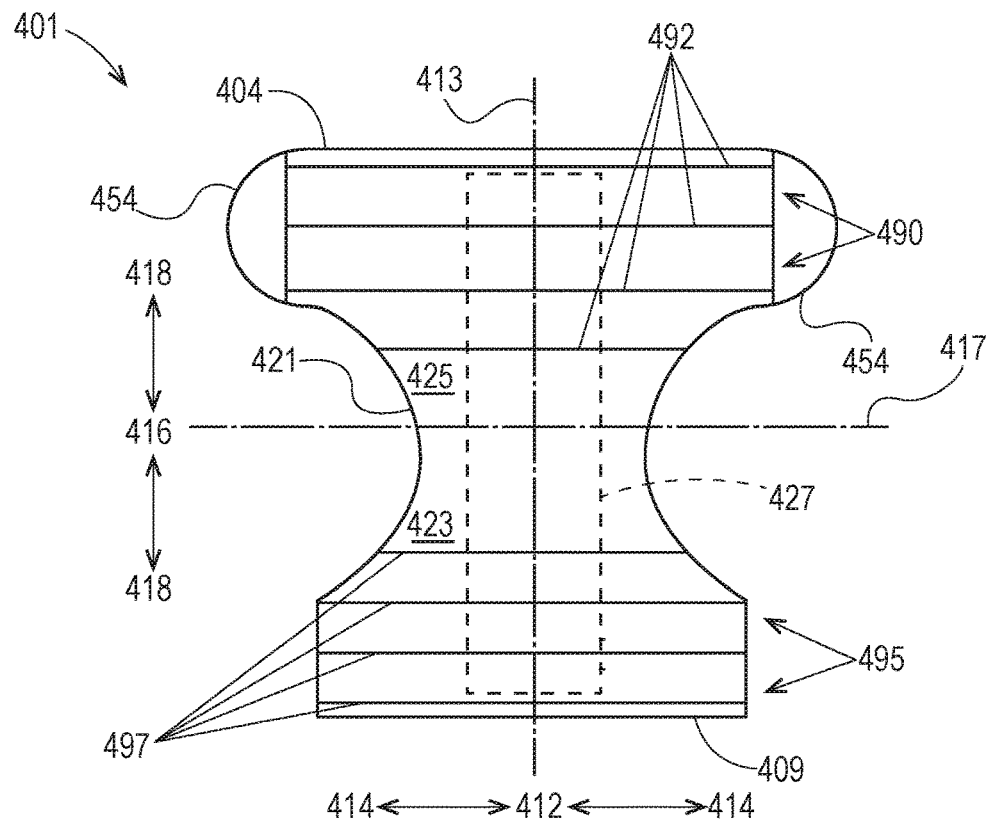
FIG. 4A illustrates a plan view of a front fastenable disposable wearable absorbent article, which includes a first embodiment of shaping elastics.

FIG. 4A illustrates a plan view of a front/side fastenable disposable wearable absorbent article 401, which includes shaping elastics 490, 495. Each of the general elements of the embodiment of FIG. 4A is configured in the same way as the like-numbered element of the embodiment of FIG. 1A. The view of FIG. 4A illustrates an inside (wearer-facing side) of the article 401 and the chassis 421.

In the article 401, a plurality 495 of front shaping elastics 497 is disposed in the front 423. In the embodiment of FIG. 4A, each of the front shaping elastics 497 is straight and parallel with the front waist edge 409 and extends laterally across the chassis of the article 401. The front shaping elastics 497 are parallel to each other and spaced apart from each other. In the article 401, a plurality 490 of back shaping elastics 492 is disposed in the back 425. In the embodiment of FIG. 4A, each of the back shaping elastics 492 is straight and parallel with the back waist edge 404 and extends laterally across the chassis of the article 401. The back shaping elastics 492 are parallel to each other and spaced apart from each other.

Figure 4B:
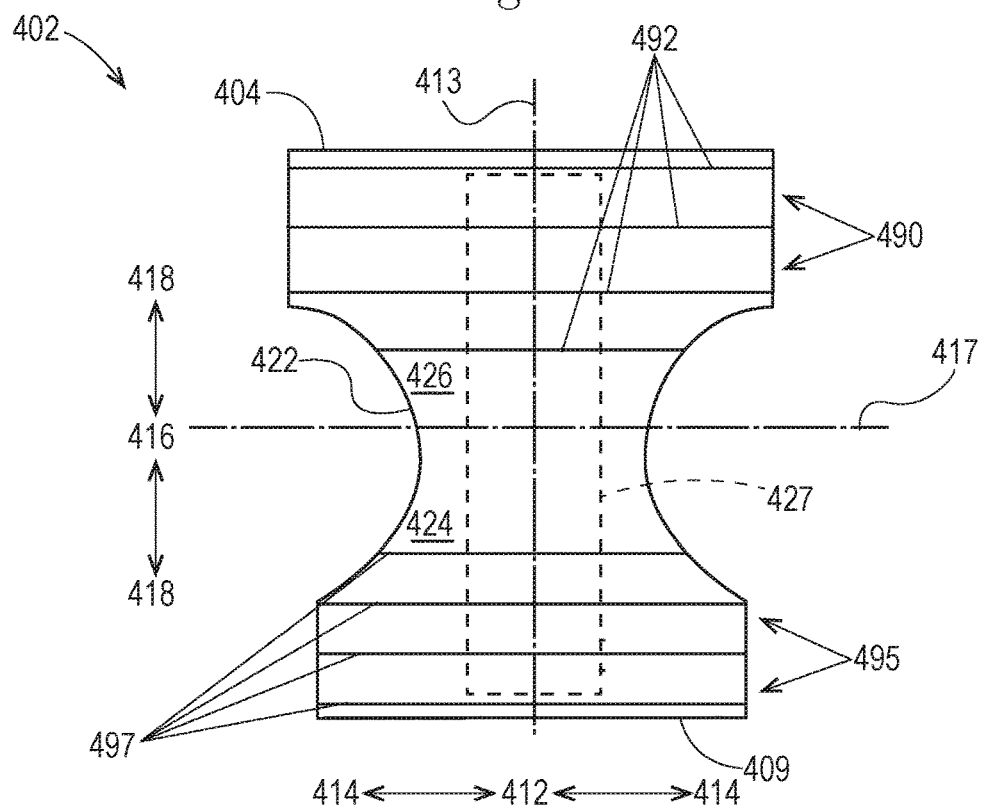
FIG. 4B illustrates a plan view of a pant type disposable wearable absorbent article, which includes the first embodiment of shaping elastics.

FIG. 4B illustrates a plan view of a pant type disposable wearable absorbent article 402, which includes pluralities of shaping elastics 490, 495. Each of the general elements of the embodiment of FIG. 4B is configured in the same way as the like-numbered element of the embodiment of FIG. 1D, and the pluralities of shaping elastics 490, 495 are configured in the same way as the like-numbered elements of the embodiment of FIG. 4A, except for differences in type of chassis. In an alternate embodiment, the pant type disposable wearable absorbent article 402 can be modified to be a belt type pant with a chassis configured in the same way as in the embodiment of FIG. 1A.

Figure 5A:
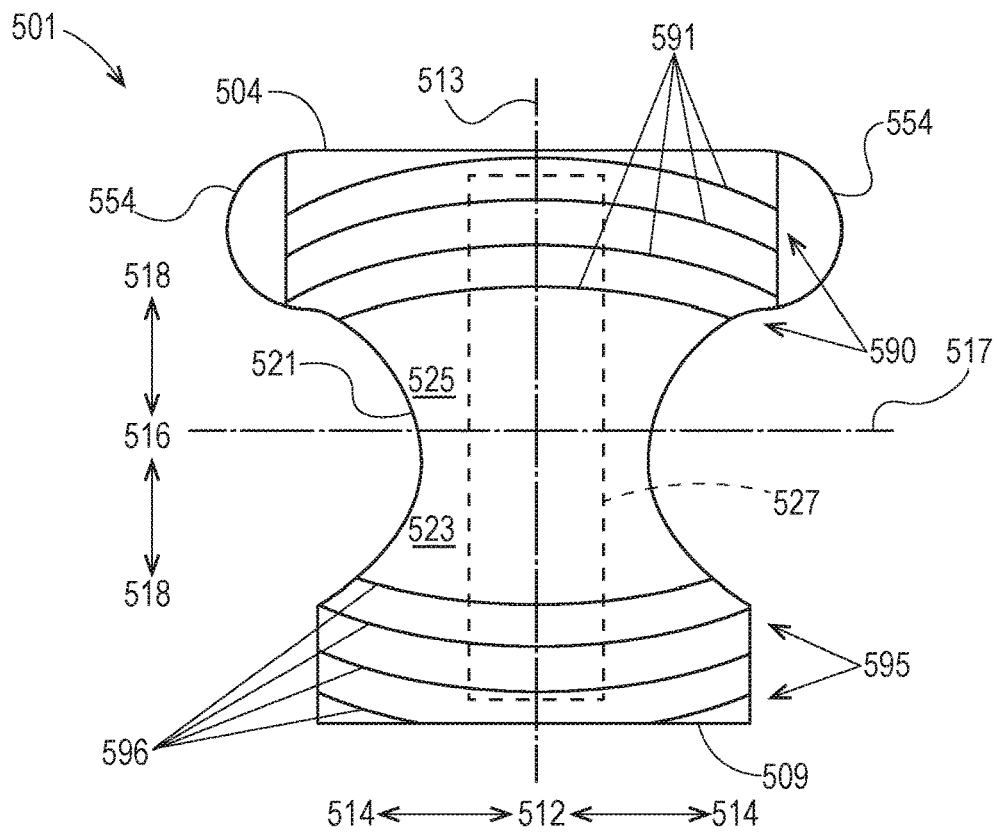
FIG. 5A illustrates a plan view of a front fastenable disposable wearable absorbent article, which includes a second embodiment of shaping elastics.

FIG. 5A illustrates a plan view of a front fastenable disposable wearable absorbent article 501, which includes pluralities of shaping elastics 590, 595. Each of the general elements of the embodiment of FIG. 5A is configured in the same way as the like-numbered element of the embodiment of FIG. 1A. The view of FIG. 5A illustrates an inside (wearer-facing side) of the article 501 and the chassis 521.

In the article 501, a plurality 595 of front shaping elastics 596 is disposed in the front 523. In the embodiment of FIG. 5A, each of the front shaping elastics 596 is curved with an overall convex shape with respect to the front waist edge 509 and extends substantially laterally across the chassis 521 of the article 501. The waist edge of one or both of the inner and outer belt portions in either one or both of the front and back waist regions may be curved either convexly with respect to the lateral centerline or concavely with respect to the lateral centerline. In such embodiments, one or more of the elastics may be curved to extend along the waist edge of the respective belt portions. In addition, the longitudinally opposing edge of the inner or outer belt portions may be curved either convexly with respect to the lateral centerline or concavely with respect to the lateral centerline. And one or more of the elastics adjacent the longitudinally opposing edge to the waist edge may be curved to extend along the longitudinally opposing edge.

The front shaping elastics 596 may be substantially concentric and spaced apart from each other. In the article 501, a plurality 590 of back shaping elastics 591 is disposed in the back 525. In the embodiment of FIG. 5A, each of the back shaping elastics 591 is curved with an overall convex shape with respect to the back waist edge 504 and extends substantially laterally across the chassis 521 of the article 501. The back shaping elastics 591 may be substantially concentric and spaced apart from each other.

Figure 5B:
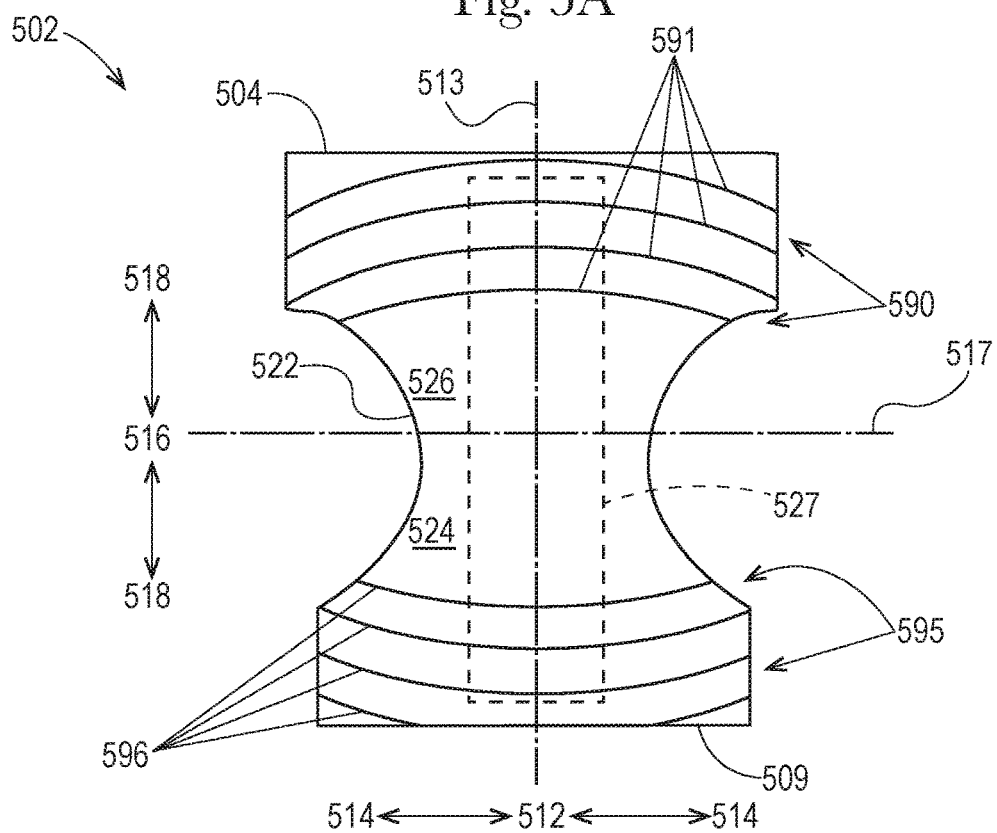
FIG. 5B illustrates a plan view of a pant type disposable wearable absorbent article, which includes the second embodiment of shaping elastics.

FIG. 5B illustrates a plan view of a pant type disposable wearable absorbent article 502, which includes pluralities of shaping elastics 590, 595. Each of the general elements of the embodiment of FIG. 5B is configured in the same way as the like-numbered element of the embodiment of FIG. 1D, and the pluralities of shaping elastics 590, 595 are configured in the same way as the like-numbered elements of the embodiment of FIG. 5A, except for differences in type of chassis. In an alternate embodiment, the pant type disposable wearable absorbent article 502 can be modified to be a belt type pant with a chassis configured in the same way as in the embodiment of FIG. 1A.

Figure 6A:
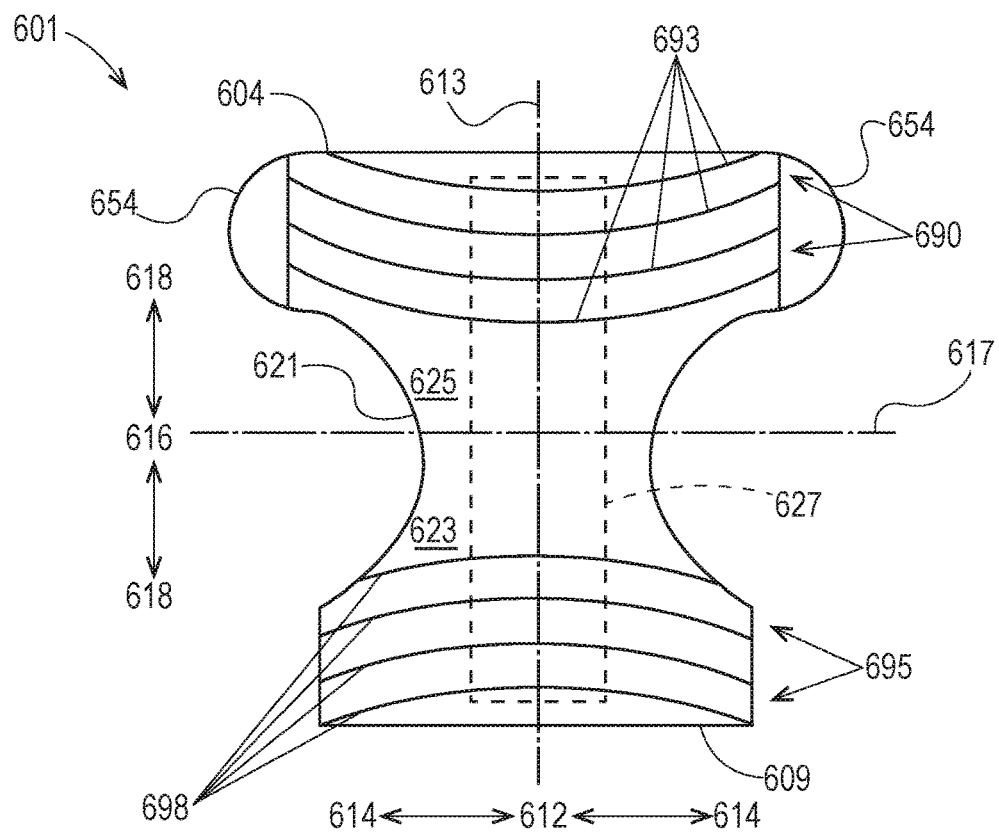
FIG. 6A illustrates a plan view of a front fastenable disposable wearable absorbent article, which includes a third embodiment of shaping elastics.

FIG. 6A illustrates a plan view of a front fastenable disposable wearable absorbent article 601, which includes pluralities of shaping elastics 690, 695. Each of the general elements of the embodiment of FIG. 6A is configured in the same way as the like-numbered element of the embodiment of FIG. 1A. The view of FIG. 6A illustrates an inside (wearer-facing side) of the article 601 and the chassis 621.

In the article 601, a plurality 695 of front shaping elastics 698 is disposed in the front 623. In the embodiment of FIG. 6A, each of the front shaping elastics 698 is curved with an overall concave shape with respect to the front waist edge 609 and extends substantially laterally across the chassis 621 of the article 601. The front shaping elastics 698 may be substantially concentric and spaced apart from each other. In the article 601, a plurality 690 of back shaping elastics 693 is disposed in the back 625. In the embodiment of FIG. 6A, each of the back shaping elastics 693 is curved with an overall concave shape with respect to the back waist edge 604 and extends substantially laterally across the chassis 621 of the article 601. The back shaping elastics 693 may be substantially concentric and spaced apart from each other.

Figure 6B:
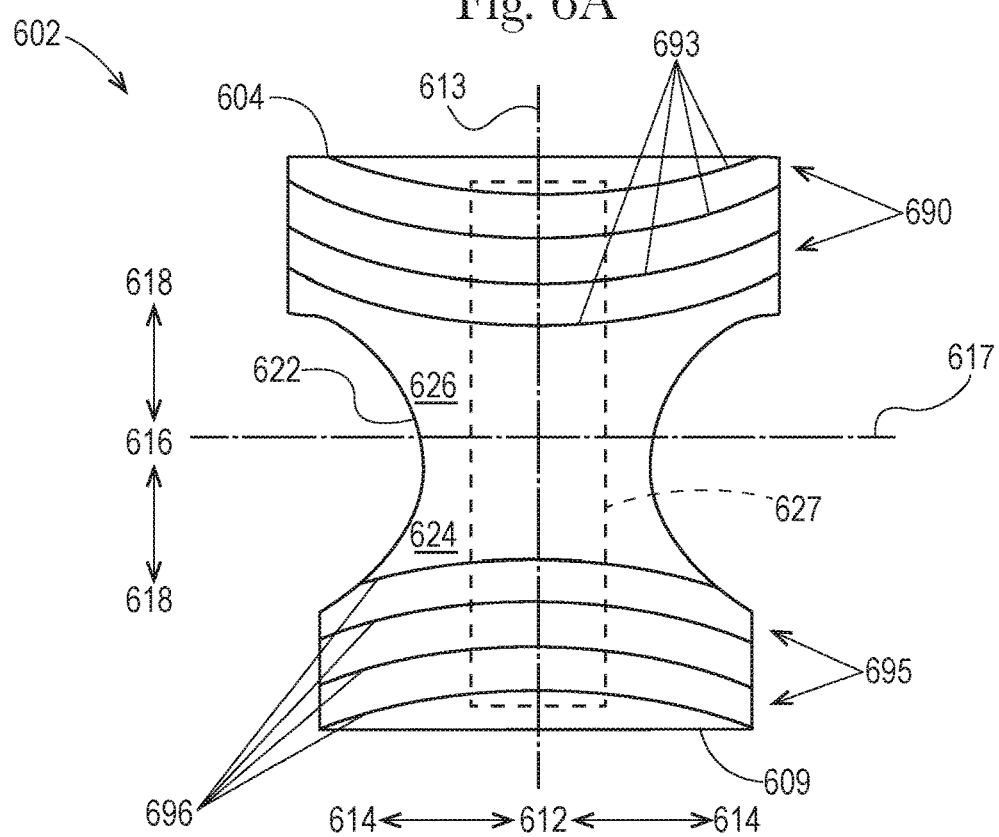
FIG. 6B illustrates a plan view of a pant type disposable wearable absorbent article, which includes the third embodiment of shaping elastics.

FIG. 6B illustrates a plan view of a pant type disposable wearable absorbent article 602, which includes pluralities of shaping elastics 690, 695. Each of the general elements of the embodiment of FIG. 6B is configured in the same way as the like-numbered element of the embodiment of FIG. 1D, and the pluralities of shaping elastics 690, 695 are configured in the same way as the like-numbered elements of the embodiment of FIG. 6A, except for differences in type of chassis. In an alternate embodiment, the pant type disposable wearable absorbent article 602 can be modified to be a belt type pant with a chassis configured in the same way as in the embodiment of FIG. 1A.

Figure 7A:
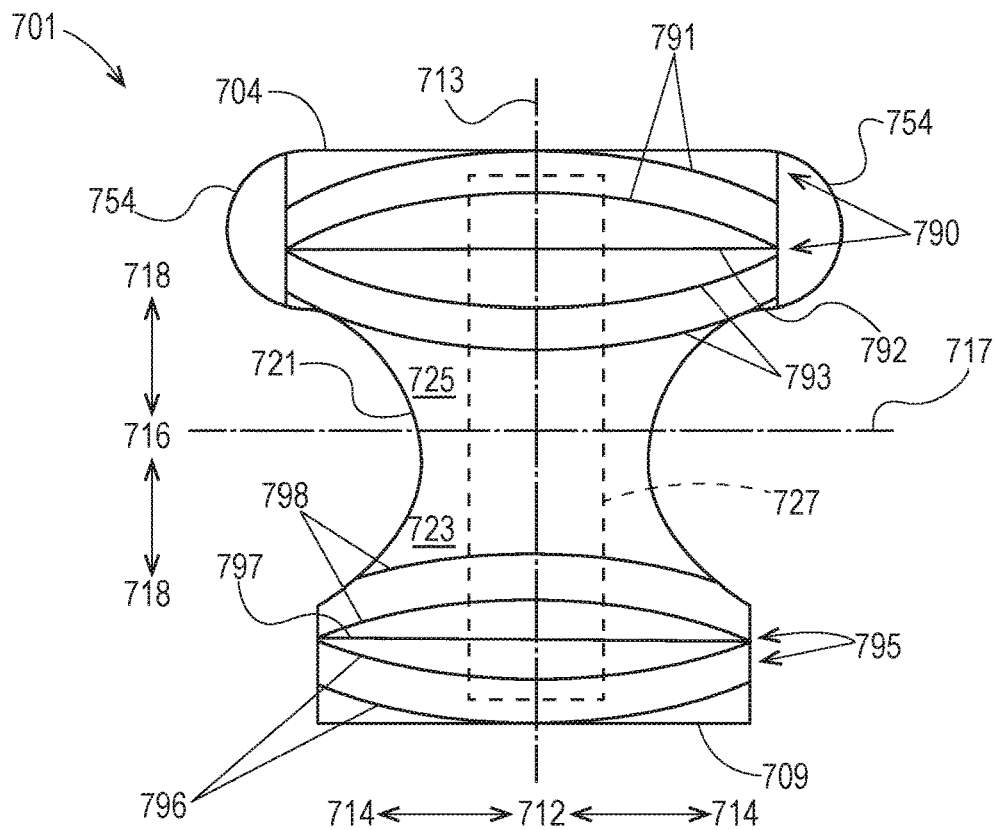
FIG. 7A illustrates a plan view of a front fastenable disposable wearable absorbent article, which includes a fourth embodiment of shaping elastics.

FIG. 7A illustrates a plan view of a front/side fastenable disposable wearable absorbent article 701, which includes pluralities of shaping elastics 790, 795. Each of the general elements of the embodiment of FIG. 7A is configured in the same way as the like-numbered element of the embodiment of FIG. 1A. The view of FIG. 7A illustrates an inside (wearer-facing side) of the article 701 and the chassis 721.

In the article 701, a plurality 795 of front shaping elastics 796, 797, and 798 is disposed in the front 723. The front shaping elastics 796 are longitudinally outboard 718 from the front shaping elastics 797, which are longitudinally outboard 718 from the front shaping elastics 798. In the embodiment of FIG. 7A, each of the front shaping elastics 796 is curved with an overall convex shape with respect to the front waist edge 709 and extends substantially laterally across the chassis 721 of the article 701, each of the front shaping elastics 797 are straight and substantially parallel with the front waist edge 709 and extends laterally across the chassis 721 of the article 701, and each of the front shaping elastics 798 is curved with an overall concave shape with respect to the front waist edge 709 and extends substantially laterally across the chassis 721 of the article 701. The front shaping elastics 796 may be substantially concentric and spaced apart from each other. The front shaping elastics 798 may be also substantially concentric and spaced apart from each other.

In the article 701, a plurality 790 of back shaping elastics 791, 792, and 793 is disposed in the back 725. The back shaping elastics 791 are longitudinally outboard 718 from the back shaping elastics 792, which are longitudinally outboard 718 from the back shaping elastics 793. In the embodiment of FIG. 7A, each of the back shaping elastics 791 is curved with an overall convex shape with respect to the back waist edge 704 and extends substantially laterally across the chassis 721 of the article 701, each of the back shaping elastics 792 is straight and substantially parallel with the back waist edge 704 and extends laterally across the chassis 721 of the article 701, and each of the back shaping elastics 793 is curved with an overall concave shape with respect to the back waist edge 709 and extends substantially laterally across the chassis 721 of the article 701. The back shaping elastics 791 may be substantially concentric and spaced apart from each other. The back shaping elastics 793 may be also substantially concentric, and spaced apart from each other.

Figure 7B:
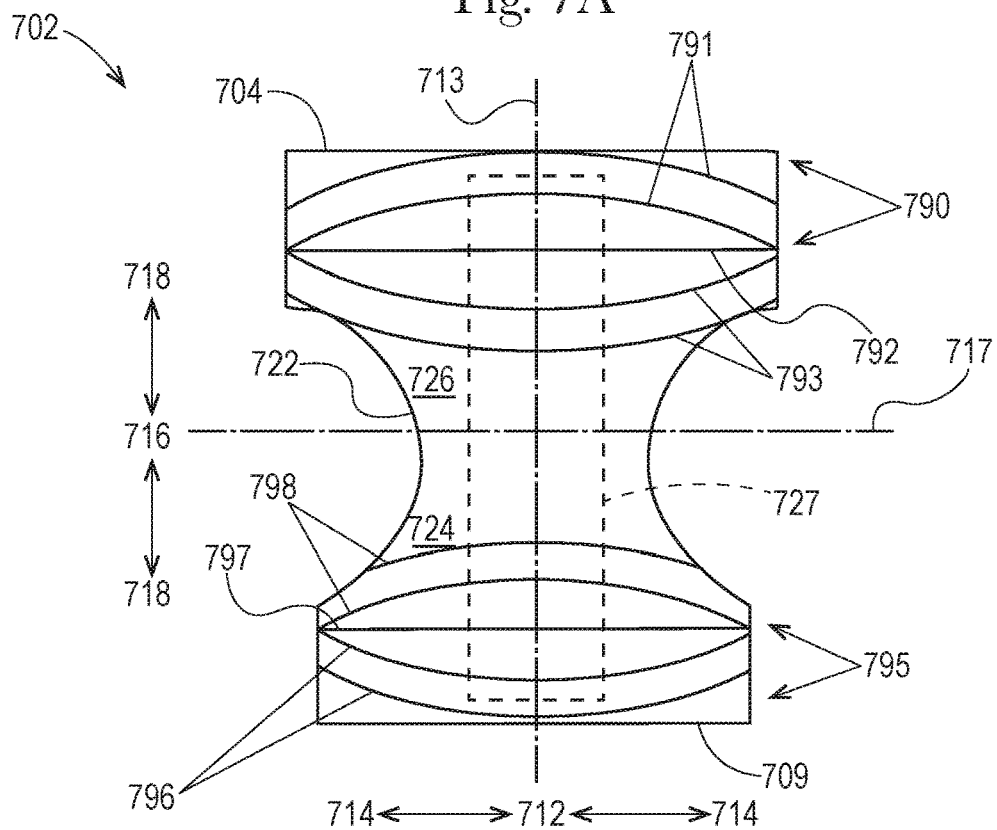
FIG. 7B illustrates a plan view of a pant type disposable wearable absorbent article, which includes the fourth embodiment of shaping elastics.

FIG. 7B illustrates a plan view of a pant type disposable wearable absorbent article 702, which includes pluralities of shaping elastics 790, 795. Each of the general elements of the embodiment of FIG. 7B is configured in the same way as the like-numbered element of the embodiment of FIG. 1D, and the pluralities of shaping elastics 790, 795 are configured in the same way as the like-numbered elements of the embodiment of FIG. 7A, except for differences in type of chassis. In an alternate embodiment, the pant type disposable wearable absorbent article 702 can be modified to be a belt type pant with a chassis configured in the same way as in the embodiment of FIG. 1A.

Figure 8A:
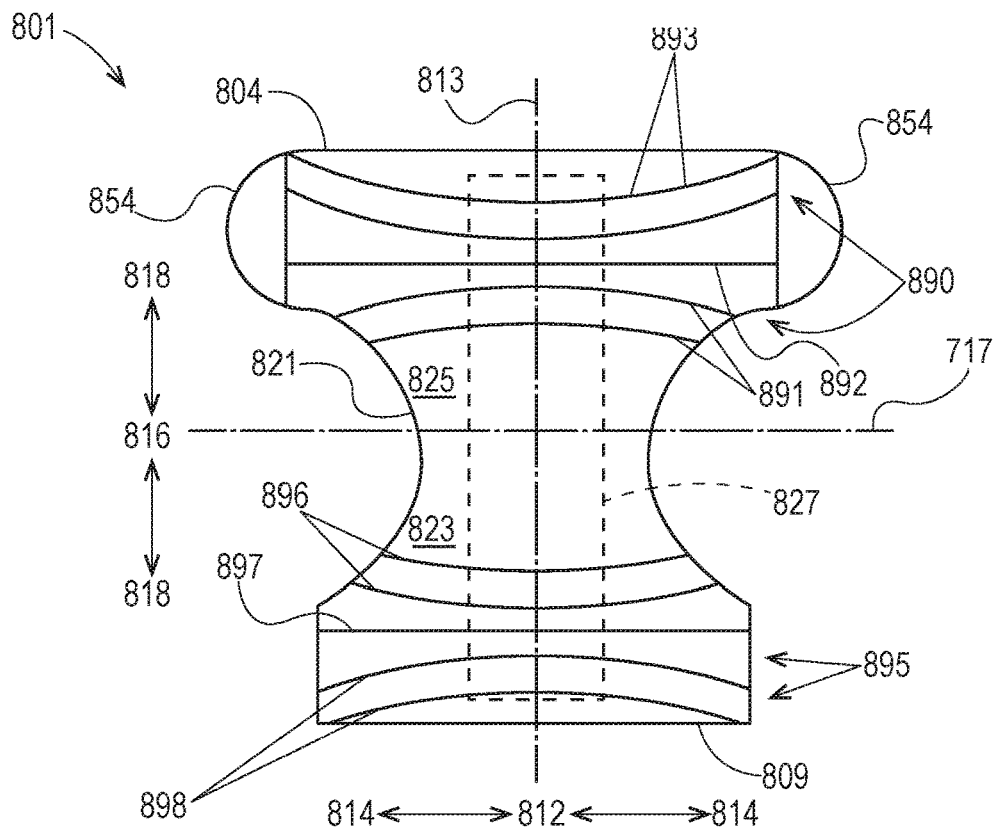
FIG. 8A illustrates a plan view of a front fastenable disposable wearable absorbent article, which includes a fifth embodiment of shaping elastics.

FIG. 8A illustrates a plan view of a front/side fastenable disposable wearable absorbent article 801, which includes shaping elastics 890, 895. Each of the general elements of the embodiment of FIG. 8A is configured in the same way as the like-numbered element of the embodiment of FIG. 1A. The view of FIG. 8A illustrates an inside (wearer-facing side) of the article 801 and the chassis 821.

In the article 801, a plurality 895 of front shaping elastics 896, 897, and 898 is disposed in the front 823. The front shaping elastics 898 are longitudinally outboard 818 from the front shaping elastics 897, which are longitudinally outboard 818 from the front shaping elastics 896. In the embodiment of FIG. 8A, each of the front shaping elastics 896 is curved with an overall convex shape with respect to the front waist edge 809 and extends substantially laterally across the chassis 821 of the article 801, each of the front shaping elastics 897 is straight and substantially parallel with the front waist edge 809 and extends laterally across the chassis 821 of the article 801, and each of the front shaping elastics 898 is curved with an overall concave shape with respect to the front waist edge 809 and extends substantially laterally across the chassis 821 of the article 801. The front shaping elastics 896 may be substantially concentric and spaced apart from each other. The front shaping elastics 898 may be substantially concentric and spaced apart from each other.

Figure 8B:
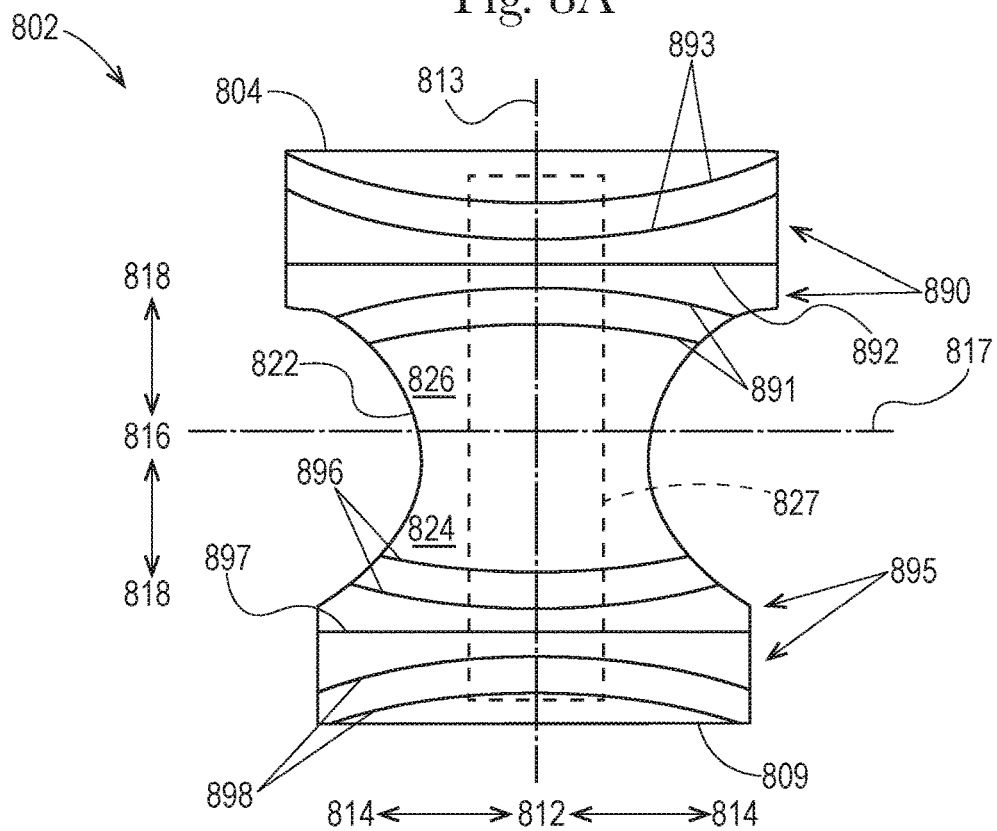
FIG. 8B illustrates a plan view of a pant type disposable wearable absorbent article, which includes a fifth embodiment of shaping elastics.

In the article 801, a plurality 890 of back shaping elastics 891, 892, and 893 is disposed in the back 825. The back shaping elastics 893 are longitudinally outboard 818 from the back shaping elastics 892, which are longitudinally outboard 818 from the back shaping elastics 891. In the embodiment of FIG. 8A, each of the back shaping elastics 891 is curved with an overall convex shape with respect to the back waist edge 804 and extends substantially laterally across the chassis 821 of the article 801, each of the back shaping elastics 892 is straight and substantially parallel with the back waist edge 809 and extends laterally across the chassis 821 of the article 801, and each of the back shaping elastics 893 is curved with an overall concave shape with respect to the back waist edge 804 and extends substantially laterally across the chassis 821 of the article 801. The back shaping elastics 891 may be substantially concentric and spaced apart from each other. The back shaping elastics 893 may be substantially concentric and spaced apart from each other. FIG. 8B illustrates a plan view of a pant type disposable wearable absorbent article 802, which includes pluralities of shaping elastics 890, 895. Each of the general elements of the embodiment of FIG. 8B is configured in the same way as the like-numbered element of the embodiment of FIG. 1D, and the pluralities of shaping elastics 890, 895 are configured in the same way as the like-numbered elements of the embodiment of FIG. 8A, except for differences in type of chassis. In an alternate embodiment, the pant type disposable wearable absorbent article 802 can be modified to be a belt type pant with a chassis configured in the same way as in the embodiment of FIG. 1A.

The embodiments of FIGS. 9A through 11B describe various anchoring systems for use in disposable wearable absorbent articles. These anchoring systems can be configured with one or more CAMs, anchoring bands, LDEs, spines, and/or other anchoring pathways, in various ways, as described herein. In FIGS. 9A through 11B, for the purpose of clarity, some parts of the disposable wearable absorbent articles are illustrated as transparent, to show structures and features, which the overlying material might otherwise hide.

With regard to anchoring, the present disclosure uses the following terminology.

The term "anchoring system" refers to one or more anchoring pathways, wherein the anchoring system can at least assist in holding a disposable wearable absorbent article in place on a wearer's body, as described herein. The term "anchoring pathway" refers to one or more anchoring elements, configured as a tension-carrying pathway, which transfers a load from the portion of the chassis comprising the absorbent core to an anchoring location on the body of wearer of the article, as described herein.

The term "anchoring elements" refers to one or more separately identifiable structural elements, which form part of an anchoring system. Some anchoring elements can be configured to collect loads from the disposable wearable absorbent article, as described herein. For example, anchoring elements can be joined to the absorbent core and/or absorbent assembly. Some anchoring elements can be configured to transfer loads in an anchoring system, as described herein. For example, anchoring elements can be configured to carry tension along an anchoring pathway. Anchoring elastics can be anchoring elements. Some anchoring elements can be configured to provide holding forces through contact with the body of a wearer at one or more anchoring locations, as described herein. The term "anchoring location" refers to a location on a wearer's body, which is capable of supporting a load transferred from an anchoring pathway, as described herein.

The term "anchored" refers to the use of an anchoring system to hold a disposable wearable absorbent article in place on the body of a wearer. When a disposable wearable absorbent article is anchored to a portion of the body of a wearer, the anchoring system is configured to at least reduce and/or prevent relative movement between article and that portion of the body, while the wearer wears the article. A disposable wearable absorbent article with an anchoring system can be anchored to a body of a wearer with one or more anchoring elements of the anchoring system configured to directly and/or indirectly (e.g. through other layers of material) overlie and/or contact one or more of various anchoring locations on parts of a body of a wearer.

A part of the body with a relatively smaller radius of curvature can, in some embodiments, act as an anchoring location that provides relatively greater friction forces, since an anchoring element can tend to wrap around such parts more tightly. This is due to the physics of a flexible material that is wrapped around a curved surface and placed under tension. In this scenario, as a tensile force places the flexible material under tension, the flexible material exerts a normal force perpendicular to and inward on the curved surface. According to the basic Capstan formula, the normal force is proportional to the tensile force divided by the radius of the curved surface. Thus, at a given tensile force, as the radius becomes smaller, the normal force becomes larger.

Also as an example, an anchoring system can be at least partially anchored by setting one or more anchoring elements on, around, and/or above one or more anchoring locations that protrude from the body, thus creating friction and/or reaction forces. A part of the body with a relatively larger horizontal protrusion can, in some embodiments, provide greater reaction forces, since an anchoring element can tend to hang and/or ride on or above such parts more securely (i.e., there is an upward component to the reaction force from the body that can support a load).

An anchoring pathway can be configured in various forms. An anchoring pathway can be made from any material suitable for carrying tensions in an anchoring system. Part, or parts, or substantially all, or all of an anchoring pathway can include one or more anchoring elements made of various suitable materials (such as a plurality of anchoring elastics). An anchoring pathway can be a unitary, continuous pathway, or can be formed by any number of anchoring elements disposed (in series or in parallel) along a pathway. Part, or parts, or substantially all, or all of an anchoring pathway (and its anchoring elements) can be straight, curved, angled, segmented, or other shapes, or combinations of any of these shapes. In some embodiments, an anchoring pathway can include one or more connecting elements, such as belts, seams, and/or fasteners.

An anchoring element can be of any suitable size, shape, and configuration. The size and/or shape of an anchoring element can be substantially or completely uniform over one or more parts of the anchoring element or over the entire length of the anchoring element, or can vary over the length of the anchoring element.

In various embodiments, anchoring elastics can be used as anchoring elements. Anchoring elastics can be formed from various materials, such as the materials described herein for shaping elastics. Anchoring elastics can have a decitex ranging from 250 to 2500, or any integer value for any decitex value in this range, or any range formed by any of these integer values.

Part, or parts, or substantially all, or all of any anchoring element can be separate from, and/or structurally associated with, and/or joined to, and/or attached to, and/or durably attached to, and/or refastenably attached to, and/or embedded in, and/or integral with one or more other elements (such as an outer cover and/or a waist cover and/or an absorbent core) of a disposable wearable absorbent article. As used herein, the term "joined" refers to configurations wherein an element is directly secured to another element and to configurations wherein an element is indirectly secured to another element by connecting the element to one or more intermediate members, which are, in turn connected to the other element.

When an anchoring pathway is formed by one or more anchoring elements embedded in or integral with one or more other elements, the anchoring pathway forms a distinct and recognizable anchoring pathway within that structure. For example, when anchoring elements that are integral with an outer cover forms an anchoring pathway, the anchoring elements can form an anchoring pathway with a substantially higher modulus of elasticity than areas of the outer cover surrounding the pathway.

Anchoring pathways disposed on surfaces within a disposable wearable absorbent article are intended to align with anatomical pathways defined on the external surfaces of a body of a wearer of the disposable wearable absorbent article in which the anchoring system is included. The shapes of the anatomical surfaces can affect the shapes of the anchoring pathways. The shapes of the anchoring pathways can, in turn, affect configurations of anchoring elements.

One kind of anchoring pathway is an anchoring band. An anchoring band can be configured to transfer tensile forces from one end to the other and to have sufficient strength to carry such tension in an anchoring system. In various embodiments, an anchoring band can at least partially encircle a lower torso of the body of the wearer, for example in the back portion of the article.

Another kind of anchoring pathway is a load distribution element (LDE). An LDE is a type of anchoring pathway that transfers loads in an anchoring system of a disposable wearable absorbent article. An LDE can receive at least some collected loads by being joined to one or more other elements of the disposable wearable absorbent article, such as an absorbent core. Also, an LDE can transfer such loads to one or more anchoring locations or anchoring pathways, such as a circumferential anchoring member (CAM) or anchoring band. In various embodiments, LDEs can be configured to transfer part, or parts, or substantially all, or all of loads from an absorbent core absorbent assembly to other portions of a disposable wearable absorbent article, for example the belt or side panels, waist elastics or leg elastics of the absorbent article.

Yet another kind of anchoring pathway is a spine. A spine is a type of anchoring band that helps support a load in the absorbent core in an anchoring system of a disposable wearable absorbent article. A spine is oriented either substantially or completely laterally or substantially or completely longitudinally. A substantial portion of a spine passes through an area of an absorbent core or absorbent assembly of a disposable wearable absorbent article. In some embodiments, substantially all or all of a spine can be contained within an area of an absorbent core.

A CAM is another kind of anchoring pathway that generally follows a curved surface within a disposable wearable absorbent article or on a body of a wearer. A CAM at least partially encircles a lower torso of the body of the wearer. In some embodiments, a CAM can substantially or completely encircle the lower torso of the body of the wearer. While a CAM may follow a curved pathway while a wearer is wearing the article, the CAM may be substantially or completely linear when the article is laid out flat.

Further, portions of the anchoring systems disclosed herein may be formed from the same elastics. For example, portions of the CAMs and LDEs may be formed from the same elastic. In other words, an elastic can be fed along the waist from the edge inward towards the longitudinal centerline and then diverted inward toward the lateral centerline to form one of the LDEs and then diverted outwardly towards the waist edge and then diverted again towards the side edge of the belt.

In FIGS. 9A through 11B, for ease of illustration, each of the anchoring pathways is shown as a unitary structure. However, each of these anchoring pathways may formed by a plurality of anchoring elements, which are anchoring elastics. In various alternate embodiments, any of these anchoring pathways can be configured in any manner described herein. Each of these anchoring systems of FIGS. 9A through 11B can be configured in a disposable wearable absorbent article to anchor an absorbent article and/or absorbent core to a wearer. In various embodiments, each of these anchoring systems can be configured in a disposable wearable absorbent article to carry part, or parts, or substantially all, or all of the loads from the absorbent core and exudates introduced into the absorbent core by the wearer of the article.

Figure 9A:
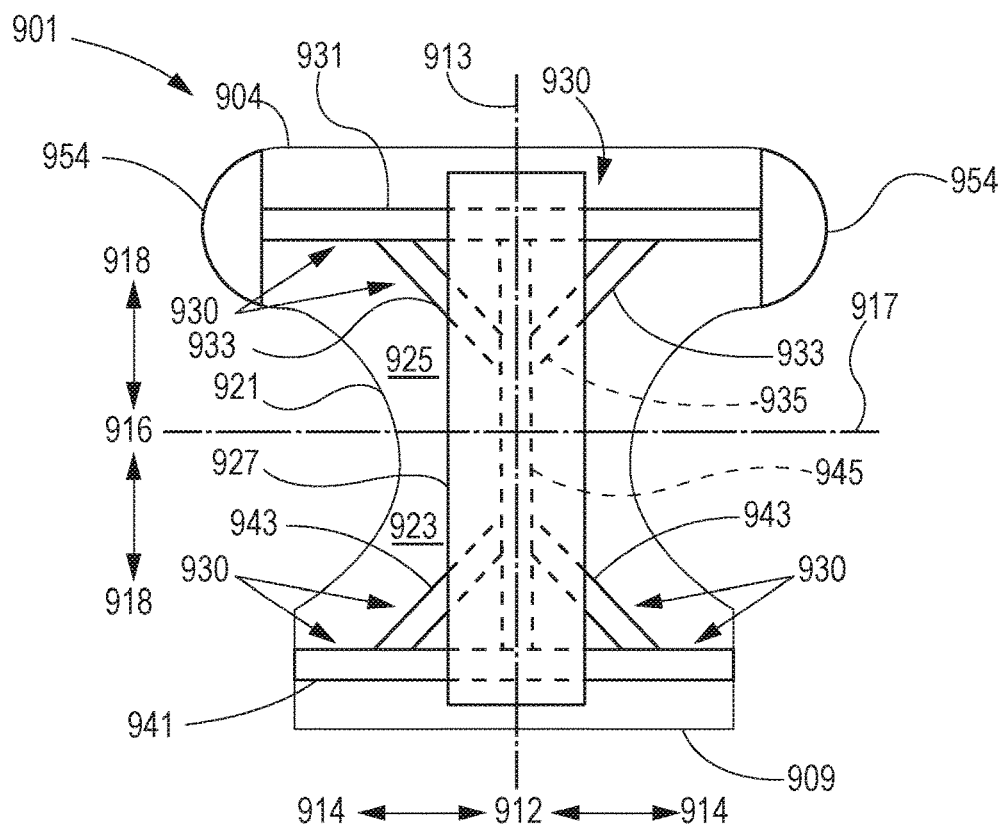
FIG. 9A illustrates a plan view of a front fastenable disposable wearable absorbent article, which includes a first embodiment of anchoring elastics.

FIG. 9A illustrates a plan view of a front/side fastenable disposable wearable absorbent article 901, which includes an anchoring system 930. Each of the general elements of the embodiment of FIG. 9A is configured in the same way as the like-numbered element of the embodiment of FIG. 1E. The view of FIG. 9A illustrates an inside (wearer-facing side) of the article 901 and the chassis 921.

The anchoring system 930 includes a back CAM 931 disposed in the back 925, back LDEs 933 disposed in the back 925, a front CAM 941 disposed in the front 923, front LDEs 943 disposed in the front 923, and a spine 935, 945. The spine 935, 945 includes a back portion of the spine 935 disposed in the back 925 and a front portion of the spine 945 disposed in the front 923. It should be noted that the LDEs 933 might be an extension of the CAM 931. In other words a portion of the CAM 931 may comprise elastic support elements that are diverted from the CAM 931 inward along the LDE 933 then outward along the opposing LDE 933 and finally along the CAM 931 on the opposing side of the product.

The back CAM 931 is disposed longitudinally inboard to and offset from the back waist edge 904. The back CAM 931 is also disposed longitudinally inboard to and offset from the longitudinally outboard back edge of the absorbent core 927. The back CAM 931 may be joined to one fastener 954 and extends laterally from that one fastener 954, laterally through a first portion of the back 925, laterally straight across, underlying, and joined to a back portion of the absorbent core 927, laterally through a second portion of the back 925, and extends laterally to the other fastener 954, joining to that other fastener 954. The back CAM 931 can be configured within the article 901 in any manner described herein. The back CAM 931 is considered a CAM because, when a wearer wears the article 901, the back CAM 931 at least partially encircles the wearer. In a first alternate embodiment, part, or parts, or substantially all, or all of the back CAM 931 could be disposed proximate to the longitudinally outboard back end of the absorbent core 927. In a second alternate embodiment, part, or parts, or substantially all, or all of the back CAM 931 could be disposed longitudinally outboard from the longitudinally outboard back end of the absorbent core 927. In a third alternate embodiment, part, or parts, or substantially all, or all of the back CAM 931 could be disposed proximate to the back waist edge 904. In a fourth alternate embodiment, part or parts of the back CAM 931 could follow one or more alternate pathways to either or both of the side ears. In a fifth alternate embodiment, part or parts of the back CAM 931 could connect to one or more additional anchoring pathways, as described herein. In a sixth alternate embodiment, the back CAM 931 may not join to one or both of the fasteners 954. In a seventh alternate embodiment, part, or parts, or substantially all, or all of the back CAM 931 may extend through or overlie the absorbent core 927. In an eighth alternate embodiment, part, or parts, or substantially all, or all of the back CAM 931 may not be joined to the absorbent core 927. In any of these alternate embodiments, part, or parts, or substantially all, or all of the back CAM 931 could be omitted. Also, in any of these alternate embodiments, one or more anchoring bands could be used along part, or parts, or substantially all, or the entire pathway of the back CAM 931.

Further, any of these alternate embodiments could be combined in whole or in part to create additional alternate embodiments.

There are two back LDEs 933, one on each side of the longitudinal centerline 913. For the back LDE 933 to the right of the longitudinal centerline, one end of the back LDE 933 connects to the back portion of the spine 935 at a location longitudinally offset from the lateral centerline 917. A portion of that back LDE 933 may underlay a portion of the absorbent core 927, and may be joined to that portion. That back LDE 933 extends straight from the back portion of the spine 935, laterally and longitudinally outward, and connects to the back CAM 931. The first back LDE 933 is considered an LDE because, when the article 901 is worn by a wearer, the first back LDE 933 is configured to transfer at least part of the load from the absorbent core 927 to the back CAM 931. The back LDE 933 on the left is configured in the same way, though mirrored by the longitudinal centerline 913. Each back LDE 933 can be configured within the article 901 in any manner described herein, including any of the alternative embodiments.

In a first alternate embodiment, a back LDE 933 could connect to the back portion of the spine 935 at a location at or proximate to the lateral centerline 917. In a second alternate embodiment, a back LDE 933 may not connect to the back portion of the spine 935, but may end at a location offset from the longitudinal centerline 913, within the area of the back portion of the absorbent core 927. In a third alternate, a back LDE 933 could connect to the back CAM 931 at a location at or proximate to the longitudinal centerline 913. In a fourth alternate, a back LDE 933 could connect to the back CAM 931 proximate to the fastener 954. In a fifth alternate embodiment, part or parts of a back LDE 933 could follow one or more alternate pathways. In a sixth alternate embodiment, part or parts of a back LDE 933 could connect to one or more additional anchoring pathways, as described herein. In a seventh alternate embodiment, part, or parts, or substantially all, or all of a back LDE 933 may extend through or overlie the absorbent core 927. In an eighth alternate embodiment, part, or parts, or substantially all, or all of a back CAM 933 may not be joined to the absorbent core 927. In any of these alternate embodiments, part, or parts, or substantially all, or all of either or both back LDEs 933 could be omitted. Also, in any of these alternate embodiments, one or more anchoring bands could be used along part, or parts, or substantially all, or the entire pathway of a back LDE 933. Further, any of these alternate embodiments could be combined in whole or in part to create additional alternate embodiments.

The front CAM 941 is disposed longitudinally inboard to and offset from the front waist edge 909 of the chassis 921. The front CAM 941 is also disposed longitudinally inboard to and offset from the longitudinally outboard front edge of the absorbent core 927. The front CAM 941 begins in one side, extends laterally from one longitudinal side edge of the chassis 921, laterally through a first portion of the front 923, laterally across, underlying, and joined to a front portion of the absorbent core 927, laterally through a second portion of the front 923, and ends in another side at another longitudinal side edge of the chassis 921. The front CAM 941 can be configured within the article 901 in any manner described herein. The front CAM 941 is considered a CAM because, when a wearer wears the article 901, the front CAM 941 at least partially encircles the wearer. When the article 901 is worn by a wearer, the front CAM 941 and the back CAM 931, together, can be considered a single CAM that completely encircles the wearer.

In a first alternate embodiment, part, or parts, or substantially all, or all of the front CAM 941 could be disposed proximate to the longitudinally outboard front end of the absorbent core 927. In a second alternate embodiment, part, or parts, or substantially all, or all of the front CAM 941 could be disposed longitudinally outboard from the longitudinally outboard front end of the absorbent core 927. In a third alternate embodiment, part, or parts, or substantially all, or all of the front CAM 941 could be disposed proximate to the front waist edge 909. In a fourth alternate embodiment, part or parts of the front CAM 941 could follow one or more alternate pathways proximate to either or both of the longitudinal sides, similar to the embodiments described for the back CAM 931. In a fifth alternate embodiment, part or parts of the front CAM 941 could connect to one or more additional anchoring pathways, as described herein. In a sixth alternate embodiment, part, or parts, or substantially all, or all of the front CAM 941 may extend through or overlie the absorbent core 927. In a seventh alternate embodiment, part, or parts, or substantially all, or all of the front CAM 941 may not be joined to the absorbent core 927. In any of these alternate embodiments, part, or parts, or substantially all, or all of the front CAM 941 could be omitted. Also, in any of these alternate embodiments, one or more anchoring bands could be used along part, or parts, or substantially all, or the entire pathway of the front CAM 941. Further, any of these alternate embodiments could be combined in whole or in part to create additional alternate embodiments.

There are two front LDEs 943, one on each side of the longitudinal centerline 913. The front LDEs 943 are configured in the same way as the back LDEs 933, though mirrored by the lateral centerline 917, and except for the differences between a back and a front of a front fastenable disposable wearable absorbent article. Each front LDE 943 can be configured within the article 901 in any manner described herein, including any of the alternative embodiments.

The back portion of the spine 935 connects to the back LDEs 933 and to the front portion of the spine 945. The back portion of the spine 935 is underlying and joined to a back portion of the absorbent core 927. The front portion of the spine 945 connects to the back portion of the spine 935 and to the front LDEs 943. The front portion of the spine 945 is underlying and joined to a front portion of the absorbent core 927. The spine 935, 945 is laterally centered on the article 901. The spine 935, 945 can be configured within the article 901 in any manner described herein.

In a first alternate embodiment, part, or parts, or substantially all, or all of the back portion of the spine 935 and/or part, or parts, or substantially all, or all of the front portion of the spine 945 could be disposed offset from the longitudinal centerline 913 and/or proximate to a laterally outboard side of the absorbent core 927. In a second alternate embodiment, part, or parts, or substantially all, or all of the back portion of the spine 935 and/or part, or parts, or substantially all, or all of the front portion of the spine 945 could be disposed outside of the area of the absorbent core 927. In a third alternate embodiment, part or parts of the back portion of the spine 935 could connect to either or both of the back LDEs 933 at one or more additional and/or alternate locations, and/or part or parts of the front portion of the spine 945 could connect to either or both of the front LDEs 943 at one or more additional and/or alternate locations. In a fourth alternate embodiment, part or parts of the back portion of the spine 935 and/or part or parts of the front portion of the spine 945 could connect to one or more additional anchoring pathways, as described herein. In a fifth alternate embodiment, the article 901 could include two or more spines, with each spine configured in any way described herein. In a sixth alternate embodiment, part, or parts, or substantially all, or all of the back portion of the spine 935 and/or part, or parts, or substantially all, or all of the front portion of the spine 945 may not be joined to the absorbent core 927. In any of these alternate embodiments, part, or parts, or substantially all, or all of the pathway of the back portion of the spine 935 and/or part, or parts, or substantially all, or all of the pathway of the front portion of the spine 945 could be omitted. In any of these alternate embodiments, one or more anchoring bands could be used along part, or parts, or substantially all, or all of the pathway of the back portion of the spine 935 and/or the front portion of the spine 945. Further, any of these alternate embodiments could be combined in whole or in part to create additional alternate embodiments.

Additionally, any of the embodiments of the front 923 of the article 901 could be combined with any of the embodiments of a back of any of the front/side fastenable disposable wearable absorbent articles, as disclosed herein or as known in the art (including a back without an anchoring system), to create further alternate embodiments. Further, any of the embodiments of the back 925 of the article 901 could be combined with any of the embodiments of a front of any of the front/side fastenable disposable wearable absorbent articles, as disclosed herein or as known in the art (including a front without an anchoring system), to create further alternate embodiments.

Figure 9B:
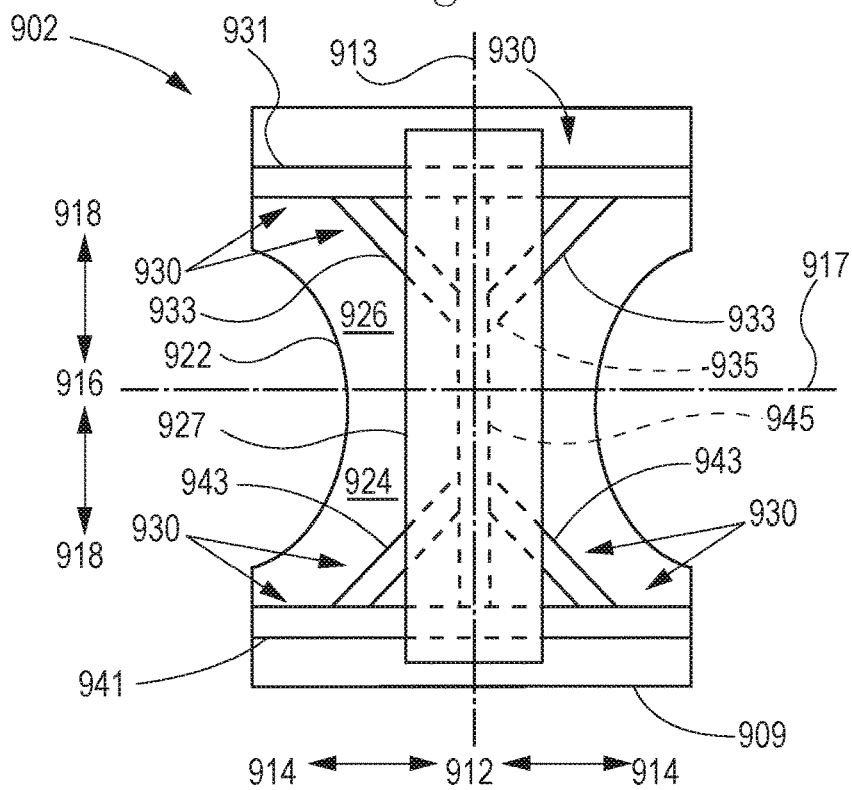
FIG. 9B illustrates a plan view of a pant type disposable wearable absorbent article, which includes the first embodiment of anchoring elastics.

FIG. 9B illustrates a plan view of a pant type disposable wearable absorbent article 902, which includes an anchoring system 930. The view of FIG. 9B illustrates an inside (wearer-facing side) of the article 902 and the chassis 922.

Each of the general elements of the embodiment of FIG. 9B is configured in the same way as the like-numbered element of the embodiment of FIG. 1D, and the elements of the anchoring system 930 are configured in the same way as the like-numbered elements of the embodiment of FIG. 9A, except for differences in type of chassis. In an alternate embodiment, the pant type disposable wearable absorbent article 902 can be modified to be a belt type pant with a chassis configured in the same way as in the embodiment of FIG. 1A.

Figure 10A:
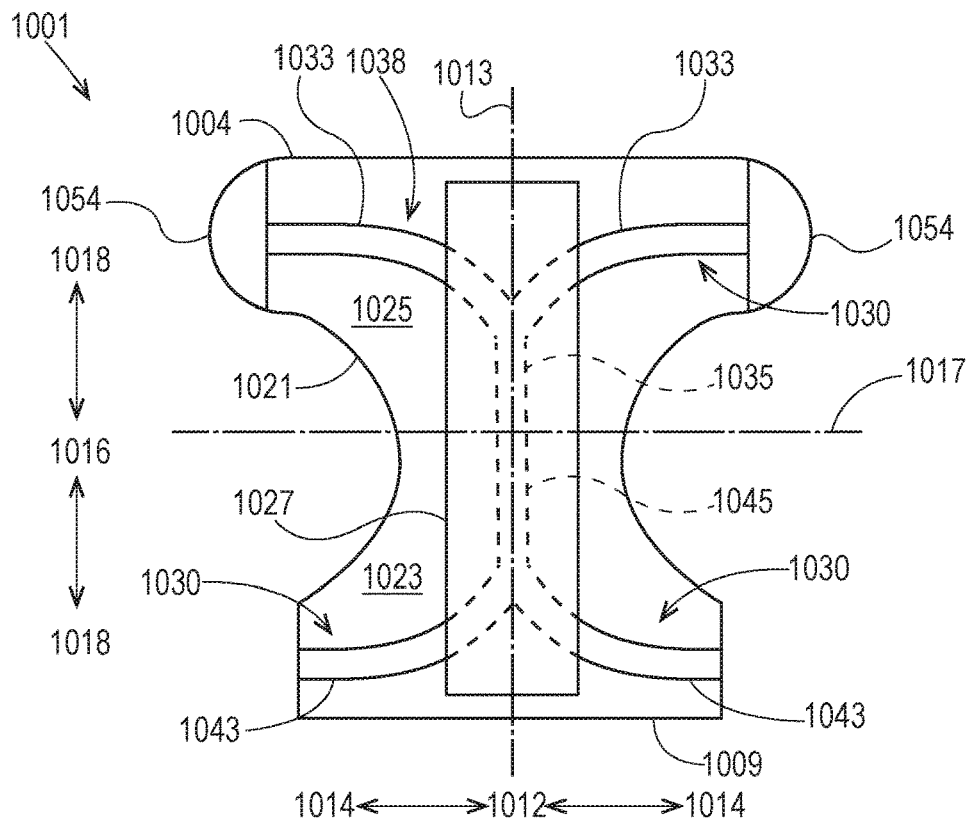
FIG. 10A illustrates a plan view of a front fastenable disposable wearable absorbent article, which includes a second embodiment of anchoring elastics.

FIG. 10A illustrates a plan view of a front/side fastenable disposable wearable absorbent article 1001, which includes an anchoring system 1030. Each of the general elements of the embodiment of FIG. 10A is configured in the same way as the like-numbered element of the embodiment of FIG. 1E. The view of FIG. 10A illustrates an inside (wearer-facing side) of the article 1001 and the chassis 1021.

The anchoring system 1030 does not include an element corresponding to the CAM 930 of FIG. 9A. Each of the back LDEs 1033 is not straight, but curved. In the embodiment of FIG. 10A, the back LDEs 1033 are curved to be convex, with respect to the back waist edge 1004, however in various embodiments, either or both of the back LDEs can be curved to be concave, with respect to the back waist edge 1004. Also, each of the back LDEs 1033 extends from the absorbent core 1027 to a portion of the longitudinal edge in a side ear. Each of the front LDEs 1043 is not straight, but curved. In the embodiment of FIG. 10A, the front LDEs 1043 are curved to be convex, with respect to the front waist edge 1009, however in various embodiments, either or both of the front LDEs can be curved to be concave, with respect to the front waist edge 1009. Also, each of the front LDEs 1043 extends from the absorbent core 1027 to a portion of the longitudinal edge in a side ear. The back LDEs 1033 and the front LDEs 1043 can be configured in any manner described herein, including any of the alternate embodiments for LDEs described in connection with FIG. 9A.

Figure 10B:
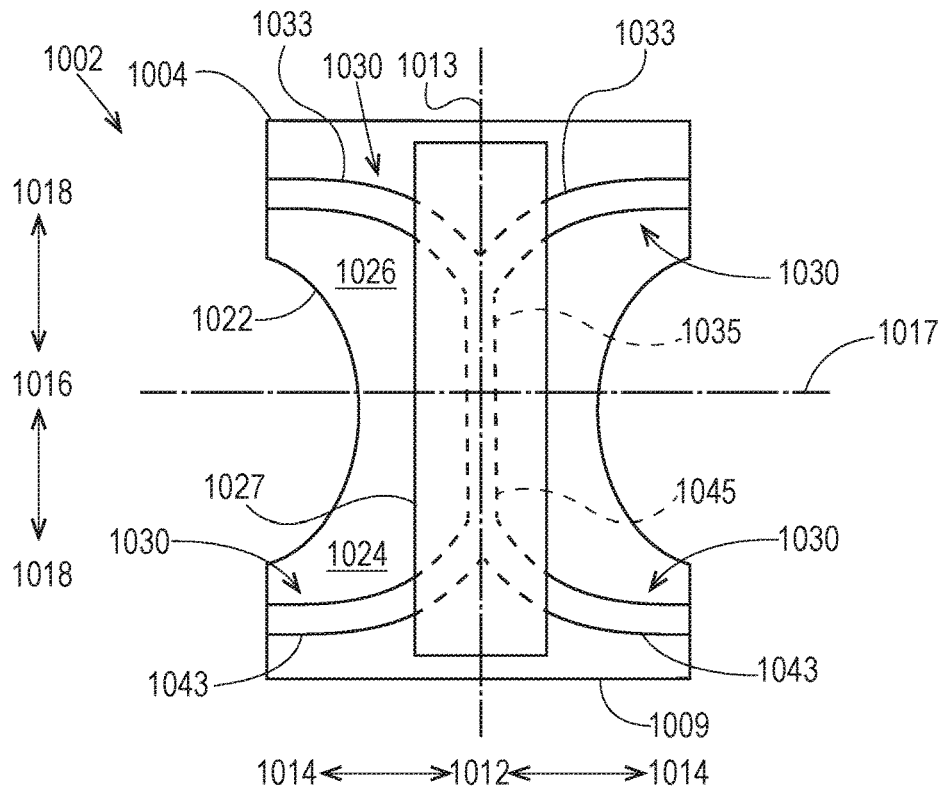
FIG. 10B illustrates a plan view of a pant type disposable wearable absorbent article, which includes the second embodiment of anchoring elastics.

FIG. 10B illustrates a plan view of an inside of a pant type disposable wearable absorbent article 1002, which includes an anchoring system 1030. The view of FIG. 10B illustrates an inside (wearer-facing side) of the article 1002 and the chassis 1022.

Each of the general elements of the embodiment of FIG. 10B is configured in the same way as the like-numbered element of the embodiment of FIG. 1D, and the elements of the anchoring system 1030 are configured in the same way as the like-numbered elements of the embodiment of FIG. 10A, except for differences in type of chassis. In an alternate embodiment, the pant type disposable wearable absorbent article 1002 can be modified to be a belt type pant with a chassis configured in the same way as in the embodiment of FIG. 1A.

Figure 11A:
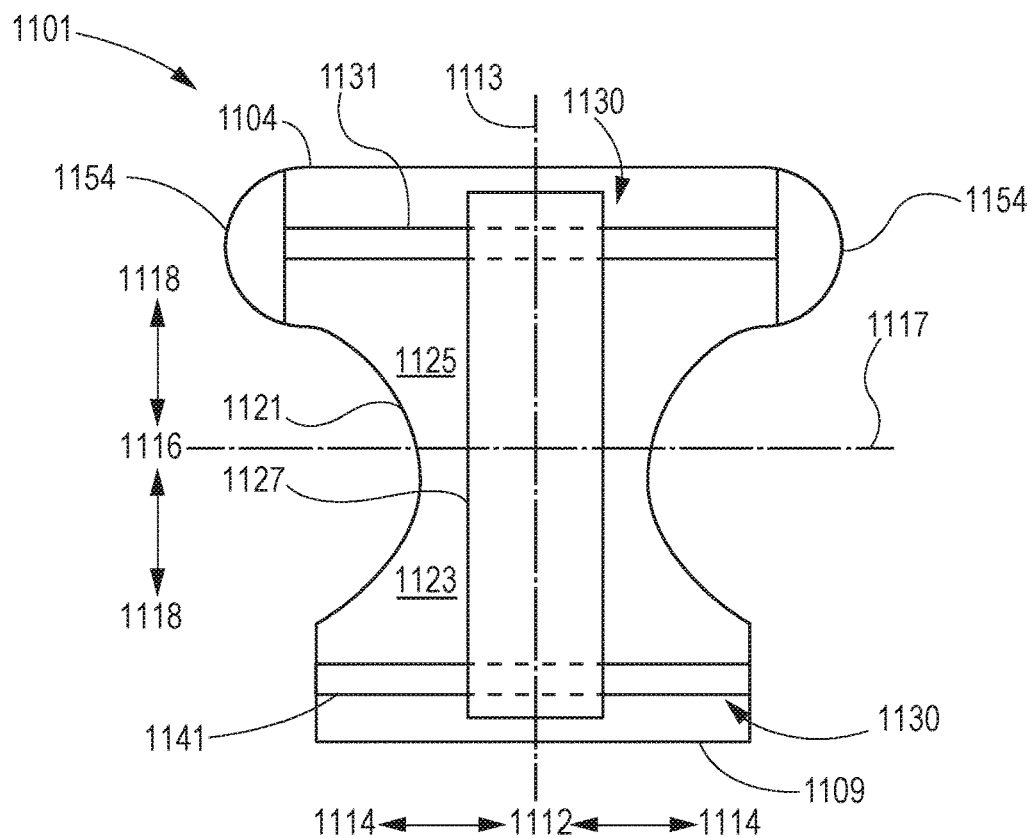
FIG. 11A illustrates a plan view of a front fastenable disposable wearable absorbent article, which includes a third embodiment of anchoring elastics.

FIG. 11A illustrates a plan view of an inside of a front/side fastenable disposable wearable absorbent article 1101, which includes an anchoring system 1130. Each of the general elements of the embodiment of FIG. 11A is configured in the same way as the like-numbered element of the embodiment of FIG. 1E. The view of FIG. 11A illustrates an inside (wearer-facing side) of the article 1101 and the chassis.

The anchoring system 1130 is does not include elements corresponding to the LDEs 933 and 943 of FIG. 9A. The anchoring system 1130 does include a front CAM 1131 and a back CAM 1161, each of which can be configured in any manner described herein for a CAM, including any of the alternate embodiments for CAMs described in connection with FIG. 9A.

Figure 11B:
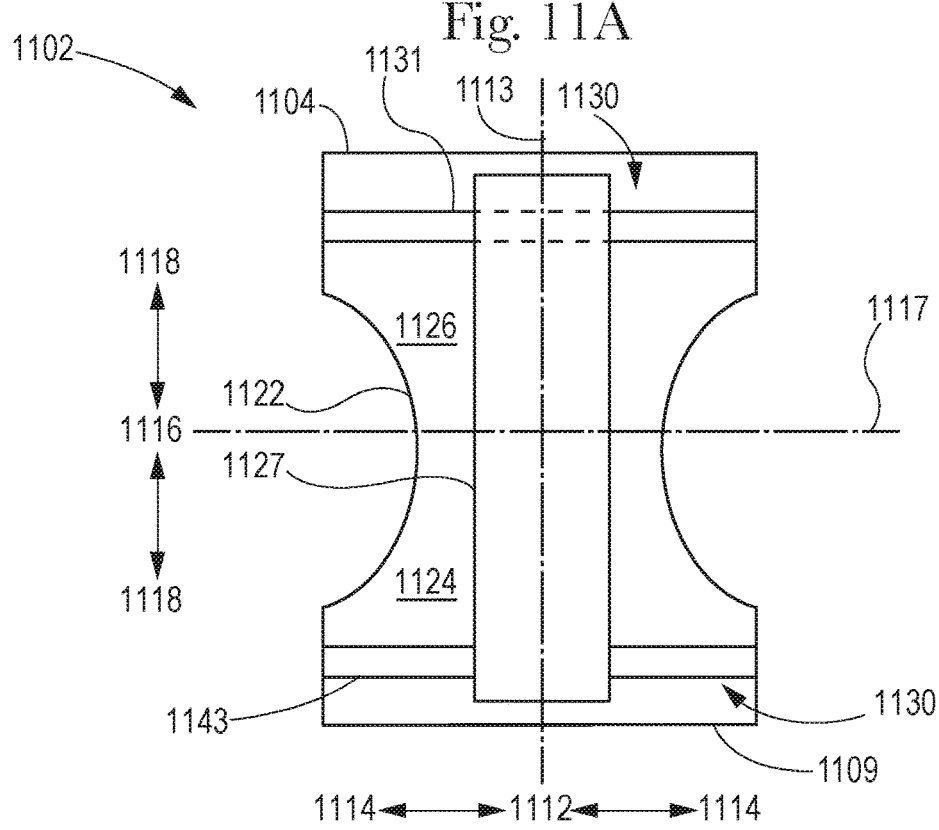
FIG. 11B illustrates a plan view of a pant type disposable wearable absorbent article, which includes the third embodiment of anchoring elastics.

FIG. 11B illustrates a plan view of an inside of a pant type disposable wearable absorbent article 1102, which includes an anchoring system 1130. The view of FIG. 11B illustrates an inside (wearer-facing side) of the article 1102 and the chassis.

Each of the general elements of the embodiment of FIG. 11B is configured in the same way as the like-numbered element of the embodiment of FIG. 1D, and the elements of the anchoring system 1130 are configured in the same way as the like-numbered elements of the embodiment of FIG. 11A, except for differences in type of chassis. In an alternate embodiment, the pant type disposable wearable absorbent article 1102 can be modified to be a belt type pant with a chassis configured in the same way as in the embodiment of FIG. 1A.

Embodiments of the present disclosure include disposable wearable absorbent articles with different elastic structures that work well together. The different elastic structures are separated into multiple layers. For example, a disposable wearable absorbent article can include shaping elastics and anchoring elastics, which are separated from each other by a layer of material. Since the shaping elastics are separated from the anchoring elastics, their functions do not conflict. The shaping elastics can at least assist in providing conforming fit and distributing contact forces over the wearer's skin while the anchoring elastics can at least assist in holding the article in place on the wearer. As a result, disposable wearable absorbent articles of the present disclosure can feel comfortable, look attractive, and perform well while wearers wear them.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document should govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a center chassis, the center chassis comprising a topsheet, a backsheet and an absorbent core, the absorbent article comprising:
    a front waist region and a front waist edge;
    a back waist region and a back waist edge;
    an inner belt portion disposed in one or both of the front waist region and back waist region, the inner belt portion comprising a first elastic;
    an outer belt portion disposed in one or both of the front waist region and back waist region, the outer belt portion comprising a second elastic;
    wherein the first elastic is formed from one or more of an elastic non-woven, elastic strands, elastic films and elastic ribbons;

wherein the second elastic is formed from one or more of an elastic non-woven, elastic strands, elastic films and elastic ribbons;

wherein at least a portion of the inner belt portion and the outer belt portion overlap;

wherein the first elastic is separated from the second elastic by a layer of material;

wherein one or both of the inner belt portion and outer belt portion comprise a layer selected from a group consisting of a nonwoven, a film, and a laminate that includes a nonwoven and a film; and wherein a portion of the inner belt portion overlaps a portion of the center chassis.

2. The absorbent article of claim 1, wherein the first elastic and the second elastic are made from different elastic materials.

3. The absorbent article of claim 1, wherein one or both of the inner belt portion and outer belt portion comprise elastic disposed in an arcuate configuration.

4. The absorbent article of claim 1, wherein the absorbent article comprises a second inner belt portion, and the second inner belt portion is disposed inwardly of the outer belt portion.

5. The absorbent article of claim 1, wherein the inner belt portion and the outer belt portion are formed in part by at least one common layer.

6. The absorbent article of claim 1, wherein the inner belt portion and the outer belt portion are separate and distinct components.

7. The absorbent article of claim 1, wherein at least one of the layers forming the outer belt portion is continuous from the front waist region to the back waist region.

8. The absorbent article of claim 1, wherein at least one of the layers forming the outer belt portion is continuous from the front waist edge to the back waist edge.

9. The absorbent article of claim 1, wherein at least one of the layers forming the inner belt portion is continuous from the front waist region to the back waist region.

10. The absorbent article of claim 1, wherein at least one of the layers forming the inner belt portion is continuous from the front waist edge to the back waist edge.

* * * * *